(12) United States Patent
Enenkel

(10) Patent No.: US 9,493,803 B2
(45) Date of Patent: *Nov. 15, 2016

(54) ARTIFICIAL INTRONS

(71) Applicant: Barbara Enenkel, Warthausen (DE)

(72) Inventor: Barbara Enenkel, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/134,177

(22) Filed: Dec. 19, 2013

(65) Prior Publication Data

US 2014/0242637 A1    Aug. 28, 2014

(30) Foreign Application Priority Data

Dec. 31, 2012 (EP) ..................................... 12199814

(51) Int. Cl.
| | |
|---|---|
| *C12N 15/113* | (2010.01) |
| *C12P 21/00* | (2006.01) |
| *C07K 16/00* | (2006.01) |
| *C12N 15/67* | (2006.01) |
| *C12N 15/85* | (2006.01) |
| *C12N 15/13* | (2006.01) |
| *C07H 21/04* | (2006.01) |
| *C12P 21/02* | (2006.01) |

(52) U.S. Cl.
CPC ................ *C12P 21/00* (2013.01); *C07K 16/00* (2013.01); *C12N 15/67* (2013.01); *C12N 15/85* (2013.01); *C07K 2317/52* (2013.01); *C07K 2319/00* (2013.01); *C07K 2319/30* (2013.01); *C12N 2830/42* (2013.01); *C12N 2830/85* (2013.01)

(58) Field of Classification Search
None
See application file for complete search history.

(56) References Cited

U.S. PATENT DOCUMENTS

| | | | |
|---|---|---|---|
| 6,010,884 A | 1/2000 | Griffiths et al. | |
| 6,972,324 B2 * | 12/2005 | Adolf et al. | 530/388.85 |
| 7,318,923 B2 * | 1/2008 | Tsurushita et al. | 424/133.1 |
| 7,320,790 B2 * | 1/2008 | Hinton et al. | 424/133.1 |
| 2005/0090648 A1 | 4/2005 | Tsurushita et al. | |
| 2008/0160048 A1 * | 7/2008 | Fuller | 424/275.1 |
| 2014/0234893 A1 | 8/2014 | Enenkel | |
| 2014/0242637 A1 | 8/2014 | Enenkel | |
| 2014/0248660 A1 | 9/2014 | Enenkel | |
| 2014/0248665 A1 | 9/2014 | Enenkel | |

FOREIGN PATENT DOCUMENTS

| | | | | |
|---|---|---|---|---|
| EP | 1 283 263 | * | 2/2003 | ............. C12N 15/12 |
| WO | 2002088307 A2 | | 11/2002 | |
| WO | 2006071804 A2 | | 7/2006 | |
| WO | 2007045465 A1 | | 4/2007 | |
| WO | 2009055656 A2 | | 4/2009 | |
| WO | 2010010108 A1 | | 1/2010 | |

OTHER PUBLICATIONS

Plantier et al., "A Factor VIII Minigene Comprising the Truncated Intron I of Factor IX Highly Improves the In Vitro Production of Factor VIII" 86 Thrombosis and Haemostasis 596-603 (2001).*
Buchman, Andrew R. et al. "Comparison of Intron-Dependent and Intron-Independent Gene Expression" Molecular and Cellular Biology, (1988) vol. 8, No. 10, pp. 4395-4405.
Neuberger, Michael S. "Expression and regulation of immunoglobulin heavy chain gene transfected into lymphoid cells" The EMBO Journal, (1983) vol. 2, No. 8, pp. 1373-1378.
Neuberger, Michael S. et al. "The Intron Requirement for Immunoglobulin Gene Expression is Dependent upon the Promoter" Nucleic Acids Research, (1988) vol. 16, No. 14, pp. 6713-6724.
International Search Report for PCT/EP2013/077024 mailed on Apr. 16, 2014.
International Search Report for PCT/EP2013/077029 mailed May 16, 2014.
International Search Report for PCT/EP2013/077042 mailed on Jul. 3, 2014.
Khamlichi, Ahmed Amine et al. "The Effect of Intron Sequences on Expression Levels of Ig cDNAs" Gene, (1994) vol. 150, pp. 387-390.
International Search Report for PCT/EP2013/0077046 mailed on Mar. 31, 2014.
Cai, X. et al., "Aberrant splicing of intron 1 leads to the heterogeneous 5' UTR and decreased expression of waxy gene in rice cultivars of intermediate amylose content." The Plant Journal, 1998, vol. 14, Issue 4, pp. 1-2.

* cited by examiner

*Primary Examiner* — Nancy J Leith
(74) *Attorney, Agent, or Firm* — Michael P. Morris; Edouard G. Lebel; Atabak R. Royaee

(57) ABSTRACT

The invention concerns the field of recombinant gene engineering. It concerns novel artificial introns and compositions comprising such introns as well as a method to improve expression of polypeptides from nucleic acids such as cloned genes, especially genes encoding antibodies and antibody derived fragments, and the production of various polypeptides in eukaryotic host cells using said novel artificial intron sequences.

20 Claims, 6 Drawing Sheets pBI-26

Figure 2
Fc-IgG1, Fc-IgG1KO
(cDNA)
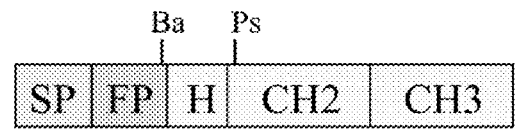
Fc-IgG1, Fc-IgG1KO
(genomic DNA)

```
                                  BglII
                                  ~~~~~~
  1    GTAAGTGCACTTTCCTAATAGATCTAATTCTAAACTCTGAGGGGGTCGGA

51    TGACGTGGCCATTCTTTGCCTAAAGCATTGAGTTTACTGCAAGGTCAGAA

101    AAGCATGCAAAGCCCTCAGAATGGCTGCAAAGAGCTCCAACAAAACAATT
151    TAGAACTTTATTAAGGAATAGGGGGAAGCTAGGAAGAAACTCAAAACATC
201    AAGATTTTAAATACGCTTCTTGGTCTCCTTGCTATAATTATCTGGGATAA
251    GCATGCTGTTTTCTGTCTGTCCCTAACATGCCCTGTGATTATCCGCAAAC
301    AACACACCCAAGGGCAGAACTTTGTTATACTAACACCATCCTGTTTGCTT
351    CTTTCCTCAG
```

(SEQ ID NO: 1)

B)

```
  1    GTACTGGCTGGATTGGGTTAGGGAAACCGAGGCGGTTCGCTGAATCGGGT

51    CGAGCACTTGGCGGAGACGCGCGGGCCAACTACTTAGGGACAGTCATGAG

101    GGGTAGGCCCGCCGGCTGCTGCCCTTGCCCATGCCCGCGGTGATCCCCAT

151    GCTGTGCCAGCCTTTGCCCAGAGGCGCTCTAGCTGGGAGCAAAGTCCGGT
201    CACTGGGCAGCACCACCCCCGGACTTGCATGGGTAGCCGCTGAGATGGA
251    GCCTGAGCACACGTGACAGGGTCCCTGTTAACGCAGTGTTTCTCTAACTT
301    TCAG
```

(SEQ ID NO: 2)

C)

```
                                  BglII
                                  ~~~~~~
  1    GTAAGTGCTGGATTGGGTTAGATCTGGAAACCGAGGCGGTTCGCTGAATC

51    GGGTCGAGCACTTGGCGGAGACGCGCGGGCCAACTACTTAGGGACAGTCA
101    TGAGGGGTAGGCCCGCCGGCTGCTGCCCTTGCCCATGCCCGCGGTGATCC
151    CCATGCTGTGCCAGCCTTTGCCCAGAGGCGCTCTAGCTGGGAGCAAAGTC
201    CGGTCACTGGGCAGCACCACCCCCGGACTTGCATGGGTAGCCGCTGAGA
251    TGGAGCCTGAGCACACGTGACAGGGTCCCTGTTAACGCAGTGTTTCTCTC
301    CCTTTCAG
```

(SEQ ID NO: 3)

Figure 5

| Fc Fusion Proteins | Vector | % Expression of cDNA (cDNA = 100 %) |
|---|---|---|
| Fc-IgG1 | pBI-26/Fc-IgG1-c | 100 |
| | pBI-26/Fc-IgG1 | 98 |
| | pBI-26/Fc-IgG1-g3 | 206 |
| Fc-IgG1KO | pBI-26/Fc-IgG1KO-c | 100 |
| | pBI-26/Fc-IgG1KO | 78 |
| | pBI-26/Fc-IgG1KO-g3 | 175 |

ARTIFICIAL INTRONS

SEQUENCE LISTING

The instant application contains a Sequence Listing which has been submitted electronically in ASCII format and is hereby incorporated by reference in its entirety. Said ASCII copy, created on Feb. 17, 2014, is named 01-2886_SL.txt and is 7,389 bytes in size.

BACKGROUND OF THE INVENTION

1. Technical Field

The invention concerns the field of recombinant gene engineering. It concerns novel introns and compositions comprising artificial introns as well as a method to improve expression of polypeptides from nucleic acids such as cloned genes, especially genes encoding antibodies and antibody-derived fragments, and the production of various polypeptides in eukaryotic host cells using said novel intron sequences.

2. Background

The market for biopharmaceuticals for use in human therapy continues to grow at a high rate with more than 300 biopharmaceuticals already approved, many more in clinical development and estimated sales of more than 167 billions by 2015. Currently, an increasing number of biopharmaceuticals is produced from mammalian cells due to their ability to correctly process and modify human proteins. Therefore the recombinant proteins are compatible with humans both functionally and pharmacokinetically. A shortcoming compared to prokaryotic expression systems is often the significantly lower protein expression level resulting in higher drug costs. Successful and high yield production of biopharmaceuticals from mammalian cells is thus crucial and is governed by various factors including host cell line, expression system, gene copy number, cell growth and productivity, secretion efficiency of the protein, culture and feed media, production and purification process, protein structure and sequence, protein stability and formulation. Expression of the recombinant protein requires an expression vector encoding the desired gene of interest. Several methods have been employed to optimize expression vectors for efficient protein production. Gene expression is regulated on transcriptional and translational levels. Hence many methods pertain to the identification and optimization of strong promoters and enhancers to improve the efficiency with which protein encoding genes are transcribed. Examples of these are the CMV immediate early promoter and enhancer, SV40 promoter and enhancer, elongation factor (EF) promoter, Polyoma enhancer, and chicken [beta]-actin promoter. Likewise, strong polyadenylation signal sequences such as bovine growth hormone (BGH) and SV40 polyadenylation sites that stabilize mRNAs and enhance transcription termination are also used to augment the protein expression from genes encoded by the expression vectors. Among the methods to improve the efficiency with which the resultant mRNA is translated are the use of translation initiation sites (AUG), optimal ribosome binding sites such as the Kozak sequence or internal ribosome entry sites (IRES) and the tripartite leader element (TPL) from adenovirus.

Another common approach to improve expression is to increase the gene copy number. This can be achieved by transfecting cells with selectable, amplifiable marker genes such as dihdrofolate reductase (DHFR) or glutamine synthetase (GS) genes and growing the cells in the presence of selective agents such as methotrexate in case of DHFR or methionine sulfoximine in case of GS.

By the chance integration of the expression vectors in the host cell genome, cells are obtained with different levels of expression of the desired gene product, as its expression is not determined solely by the strength of the transcriptional and translational regulatory elements described above. The chromatin structure present at the integration site can affect the level of expression both negatively and positively. Increasingly, therefore, cis-active elements which positively influence the expression at the chromatin level are integrated in expression vectors. These include locus control regions (LCR), scaffold/matrix attachment regions (S/MARs), ubiquitous chromatin opening elements (UCOE), expression augmenting sequence elements (EASE), transcription or expression enhancing elements (TE element) or stimulatory and anti-repressor elements (STAR).

Even though there exist prior art elements to increase the protein expression by modulating the expression vector, there is further need to identify regulatory elements to further increase the productivity of a recombinant production cell line.

SUMMARY OF THE INVENTION

It is an objective of this invention to provide mammalian gene expression vectors for driving strong and stable gene expression in eukaryotic cells.

To achieve this objective the present invention provides novel sequences, expression vectors and a method of producing higher levels of recombinant proteins in eukaryotic cells, which pertains to the use and selection of non coding sequence elements such as introns. Introns normally form an integral part of eukaryotic genes as intervening sequences between exons. They are precisely deleted from the primary transcript by a process known as RNA splicing to form mature messenger RNA (mRNA). RNA splicing is one of the main mechanisms of qualitative and quantitative regulation of gene expression in eukaryotic genomes. Alternative splicing is a major mechanism for the enhancement of transcriptome and proteome diversity. By inclusion of different exons in the mRNA multiple transcripts are obtained from the same gene. However, splicing has also an impact on transcription, mRNA export, mRNA stability and even protein translation. Because of the beneficial effect of the intron during post-transcriptional processes, the complementary DNA (cDNA) version of most natural intron-containing genes, for example immunoglobulin genes, is expressed quite poorly in mammalian cells even if strong transcriptional promoters are used for expression. The presence of cryptic splice sites in the gene sequences can lead to alternative splicing events, especially in intron-containing genes, and thus aberrant gene expression. This might lead to unwanted by-products with altered protein sequences and thus properties and functions. A variety of algorithms might be used to identify putative splicing sites in terms of probability of usage but the success varies. The probability of aberrant splicing events can be lowered by using a cDNA version of the gene of interest. cDNAs are also preferred if the genomic versions of the genes are too large in size to incorporate them into useful expression vectors. The downside is frequently a lower expression of the protein of interest. This is routinely overcome by the optimization of the cDNA sequences thereby removing cryptic splice sites, direct repeats, secondary structure elements and other motifs interfering with expression. Also, the GC content for improved RNA stability and the codon usage are routinely optimized. The process of gene optimization is routinely performed on sequences without introns. In general, it is challenging to improve the level of recombinant gene expression in eukaryotic cells. Frequently, due to the reasons above, introns within the coding regions are not used to increase recombinant gene expression of genes, which encode proteins of interest, but such proteins of interest are routinely expressed as cDNAs having no introns at all.

The present invention solves this problem by providing novel introns and methods of preparing and selecting mammalian cell lines which allow a high expression of heterologous gene products, preferably biopharmaceutically relevant polypeptides or proteins. Surprisingly, it has been found that these newly identified introns outperform the natural genomic DNA set-up as well as the corresponding cDNA set-up with optimized nucleotide sequences and lead to higher productivity of producer cells.

The present invention provides intron sequences that increase the expression of heterologous nucleotide sequences encoding products of interest such as antibodies, enzymes, hormones, receptors, cytokines, lymphokines, adhesion molecules and derivatives or fragments thereof, in a eukaryotic host cell. The intron sequences of the present invention have the advantageous technical effect that the expression of transcription units into which these intron sequences are placed is increased (see FIG. 5).

The present invention provides artificial intron sequences placed into nucleotide sequences at the position of native intron(s) in a native eukaryotic gene. Preferably, they are introduced in a way that functional and efficient splice donor site and functional and efficient splice acceptor site are obtained.

In native immunoglobulin genes of for example mouse or human origin the introns are located in the following positions within the transcription units:

within the codon encoding the amino acid at position −4 (counting backwards from the 3' end of the amino acid sequence of the signal peptide) of the signal peptide sequence of both heavy and light chains between the first and second nucleotide of the codon within the codon encoding the first amino acid at position 108 in the constant domain CL of kappa and lambda light chains between the first and second nucleotide of the codon within the codon encoding the first amino acid at position 118 in the constant domain CH1 of heavy chains between the first and second nucleotide of the codon within the codon encoding the first amino acid at position 216 in the hinge region of heavy chains between the first and second nucleotide of the codon within the codon encoding the first amino acid at position 231 in the constant domain CH2 of heavy chains between the first and second nucleotide of the codon within the codon encoding the first amino acid at position 341 in the constant domain CH3 of heavy chains between the first and second nucleotide of the codon In the present invention the artificial intron is replacing the native intron within the first codon of a constant CH1 domain of a human immunoglobulin or within the first codon of a constant CH2 domain of a human immunoglobulin whereby these domains are located in transcription units coding for an antibody or an antibody-derived fragment. Or the artificial intron is replacing the native intron in a nucleotide sequence coding for a signal peptide sequence such as an immunoglobulin signal peptide.

Numbering of the amino acids in the variable regions of heavy and light chain and in the constant domains of the light chains is according to Kabat et al. (1991), "Sequences of proteins of immunological interest", US Dept. Health and Human Services, and numbering of the constant domains and hinge regions of the heavy chains according to the EU index in Kabat et al. (1991).

DESCRIPTION OF THE FIGURES

FIG. 1 schematically shows the design of the expression vector pBI-26 used for the transfection of CHO-DG44 cells. "P/E" means a composite unit that contains both CMV enhancer and promoter element, "P" on its own a promoter element and "T" a termination signal for transcription, which is required for polyadenylation of transcribed messenger RNA. For cloning of the gene of interest a sequence region with multiple cutting sites for restriction endonucleases (multiple cloning sites—"mcs") is inserted after the promoter/enhancer element. For termination of the transcript of the gene of interest the termination signal of the hamster growth hormone is used. The amplifiable selectable marker dihydrofolate reductase is abbreviated to "dhfr" and is under the control of the promoter and termination signal of the hamster dhfr gene. The position and direction of transcription initiation within each transcription unit is indicated by an arrow.

FIG. 2: GENE STRUCTURE OF GENES OF INTEREST IN CONTROL VECTORS

FIG. 2 schematically shows the gene structure of the genes of interest encoded in the recombinant control vectors. The genes encoding Fc fusion proteins are either cloned as cDNA or as genomic DNA versions. The constant domains derived from a human antibody heavy chain of IgG1 isotype are abbreviated to "CH2" and "CH3" and the hinge region to "H". Introns are abbreviated to "I", signal peptide sequences to "SP" and the fusion partner of the Fc fusion proteins to "FP". In the genomic DNA the native intron is in its natural position located within the codon encoding for the first amino acid of the constant domain CH3. Restriction enzyme sites for subcloning of intron sequences into new positions are "Ba" (=BamHI) and "Ps" (=PspOMI). The Fc fusion protein is abbreviated to "Fc". "KO" means that the constant domain CH2 of human IgG1 origin contains the amino acid substitutions Leu234Ala and Leu235Ala (numbering of the amino acids in the constant domains according to the EU index in Kabat et al. (1991), "Sequences of proteins of immunological interest", US Dept. Health and Human Services.).

FIG. 3: INTRON SEQUENCES

FIG. 3 shows the nucleotide sequences of the (A) de novo synthesized modified intron of a human antibody kappa light chain (SEQ ID NO: 1), the (B) dihyrdofolate reductase intron (SEQ ID NO: 2) derived from the Chinese hamster (*Cricetus griseus*) and the (C) de novo synthesized modified dihydrofolate reductase intron (SEQ ID NO: 3) derived from the Chinese hamster (*Cricetus griseus*). The intron located splice acceptor site is underlined with a broken line, the intron located part of the splice donor site with a solid line and the putative branch site with a double line. The 5' region of the modified kappa intron and the 5' region of the modified dihydrofolate reductase intron contain a single restriction enzyme site for BglII which can be used for cloning purposes. Boxed nucleotides indicate the first triplets which could act as a stop codon in each of the three possible reading frames in case splicing of the intron at the splice donor site does not occur.

FIG. 4 shows schematically the gene structure of the Fc fusion protein genes in which the artificial intron has been positioned within the codon encoding the conserved amino acid alanine in position 231 of the constant domain CH2. The constant regions of the Fc region from a human IgG1 heavy chain are abbreviated to "CH2" and "CH3" and the hinge region to "H". The intron is abbreviated to "I", the signal peptide sequence to "SF" and the fusion partner of the Fc fusion proteins to "FP". "KO" means that the constant domain CH2 of human IgG1 origin contains the amino acid substitutions Leu234Ala and Leu235Ala. Numbering of the amino acids in the constant domains and hinge regions of the heavy chain is according to the EU index in Kabat et al. (1991), "Sequences of proteins of immunological interest", US Dept. Health and Human Services.

The nucleotide sequences of the exon/artificial intron and artificial intron/exon boundaries as well as the immediate nucleotide sequences flanking these boundaries are shown below. Capital letters indicate the nucleotides of the coding region and small letters the non-coding nucleotides within the artificial intron region. Splice donor sites and splice acceptor sites are underlined with solid lines and broken lines, respectively. Restriction enzyme sites are marked with bold letters and the corresponding restriction enzyme is indicated below. The predicted amino acids (3-letter code) in the coding regions are shown above the coding nucleotide sequence. Genes contain either the modified human kappa light chain intron with SEQ ID NO: 1 marked with suffix "g3", the hamster dhfr intron with SEQ ID NO: 2 marked with suffix "g11" or the modified hamster dhfr intron with SEQ ID NO:3 marked with suffix "g12". The black arrow indicates the border between hinge region and the CH2 domain. FIG. 4 shows nucleotides 1-6 and 346-360 of the "kappa intron (SEQ ID NO:1)", nucleotides 1-6 and 290-304 of the "dhfr intron (SEQ ID NO:2)" and nucleotides 1-6 and 294-308 of the "dhfr intron (SEQ ID NO:3)".

FIG. 5: IMPACT OF ARTIFICIAL INTRON ON EXPRESSION OF FC FUSION PROTEINS

In two independent series CHO-DG44 cells are co-transfected (n=3) with expression vectors encoding various Fc fusion protein gene formats. The Fc part of the fusion protein is derived form a human IgG1 and contains the C-terminal part of the hinge region and the CH2 and CH3 domain. "KO" means that the constant domain CH2 of human IgG1 origin contains the amino acid substitutions Leu234Ala and Leu235Ala (numbering of the amino acids in the constant domains and hinge regions of the heavy chains is according to the EU index in Kabat et al. (1983), "Sequences of proteins of immunological interest", US Dept. Health and Human Services.). Genes in the expression vectors are either cloned as cDNA, marked with the suffix "c", or as genomic DNA versions (no suffix). In the latter the introns are contained in their natural positions within the first codon of the CH3 domain. Placement of the modified human kappa light chain intron with SEQ ID NO: 1 within the codon encoding the first conserved amino acid alanine of the CH2 domain at position 231 is marked with the suffix "g3".

After a period of 48-72 hours the protein titers in the supernatants are determined by ELISA. To correct for transfection efficiency cells are co-transfected with a plasmid encoding secreted alkaline phosphatase (SEAP) as reporter protein and the SEAP activity is measured. The average Fc fusion protein titers obtained are used to calculate the percentage of expression whereby the cDNA setting within each transfection series is taken as 100%. The highest protein expression is obtained from the artificial intron-containing gene sequences containing the modified human kappa light chain intron.

Figure 6:
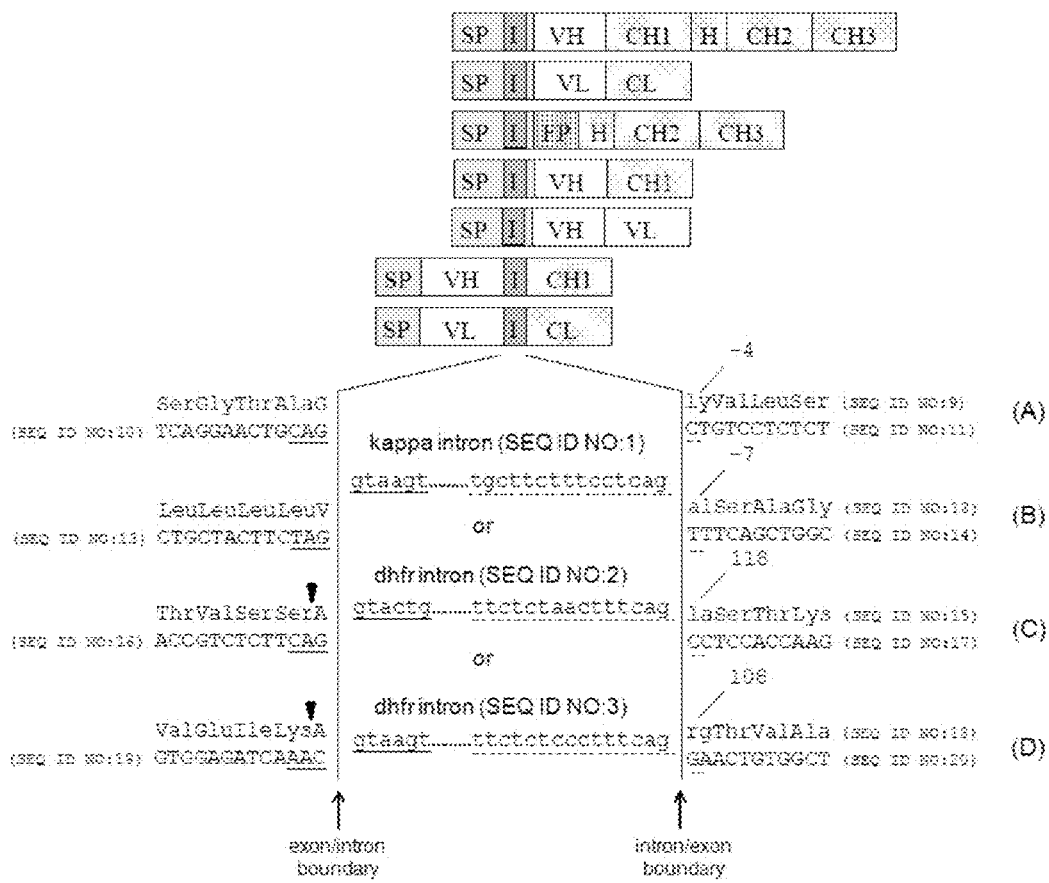

FIG. 6: POSITION OF ARTIFICIAL INTRONS IN SEQUENCES OF ANTIBODIES AND ANTIBODY-DERIVED FRAGMENTS

FIG. 6 shows schematically the gene structure of heavy chain antibody genes or antibody-derived fragments in which the artificial introns have been positioned (A) in the native intron positions of immunoglobulin signal peptides of mouse heavy chain (within the codon encoding the amino acid at position −4 counting backward from the 3' end of the amino acid sequence of the signal peptide), (B) in the native intron position of a human Fc gamma receptor III signal peptide (within the codon encoding the amino acid at position −7 counting backward from the 3' end of the amino acid sequence of the signal peptide), (C) in the native intron position of constant immunoglobulin domains CH1 of human origin (within the codon encoding the first amino acid at position 118) or (D) in the native intron position of the constant immunoglobulin kappa domains CL of human origin (within the codon encoding the first amino acid at position 108). The constant regions of antibody heavy chain of IgG1, IgG2 or Ig4 isotype are abbreviated to "CH1", "CH2" and "CH3" and the hinge region to "H". "VH" means the variable region of an antibody heavy chain and "VL" means the variable region of an antibody light chain. The intron is abbreviated to "I", the signal peptide sequence to "SF" and the fusion partner of the Fc fusion proteins to "FP". Numbering of the amino acids in the variable regions of heavy and light chain and in the constant domains of the light chains is according to Kabat et al. (1991), "Sequences of proteins of immunological interest", US Dept. Health and Human Services, and numbering of the constant domains and hinge regions of the heavy chains according to the EU index in Kabat et al. (1991). The nucleotide sequences of the exon/artificial intron and artificial intron/exon boundaries are shown below. Capital letters indicate the nucleotides of the coding region and small letters the non-coding nucleotides within the artificial intron region. Splice donor sites and splice acceptor sites are underlined with solid lines and broken lines, respectively. The predicted amino acids (3-letter code) in the coding regions are shown above the coding nucleotide sequence. Genes contain either the modified human kappa light chain intron with SEQ ID NO: 1, the hamster dhfr intron with SEQ ID NO: 2 or the modified hamster dhfr intron with SEQ ID NO:3. FIG. 6 shows nucleotides 1-6 and 346-360 of the "kappa intron (SEQ ID NO:1)", nucleotides 1-6 and 290-304 of the "dhfr intron (SEQ ID NO:2)" and nucleotides 1-6 and 294-308 of the "dhfr intron (SEQ ID NO:3)".

DETAILED DESCRIPTION OF THE INVENTION

FIG. 5 shows the impact of an artificial intron on the expression of Fc fusion proteins. Two independent transient transfection series were performed in triplicate. Surprisingly, the intron-containing gene set-ups in which a artificial modified single intron sequence derived from a human kappa gene (SEQ ID NO: 1, FIG. 3A) is placed in the codon encoding the first amino acid of the constant domain CH2 within the Fc fusion gene are outperforming the corresponding cDNA versions by a factor of 1.8-2.1. In contrast, cells transfected with the genomic DNA with a natural intron in the codon for the first amino acid of the CH3 domains as found in the natural immunoglobulin genes show an expression performance comparable to the cDNA setting or even lower.

The general embodiments "comprising" or "comprised" encompass the more specific embodiment "consisting of". Furthermore, singular and plural forms are not used in a limiting way.

Terms used in the course of this present invention have the following meaning.

The terms "intron" as used herein, refer to a non-coding or intervening polynucleotide sequence of varying length, normally present within many eukaryotic genes, which is removed from a newly transcribed mRNA precursor by the process of splicing for which highly conserved sequences at or near either end of the intron are necessary. In general, the process of splicing requires that the 5' and 3' ends of the intron be correctly cleaved and the resulting ends of the mRNA be accurately joined, such that a mature mRNA having the proper reading frame for protein synthesis is produced. Many splice donor and splice acceptors sites, meaning the sequences immediately surrounding the exon-intron- and intron-exon-boundaries, have been characterized and described and are known to the skilled artisan. Normally, the sequence of mammalian introns begins with GT and ends with AG with a few minor introns starting with AT and ending with AC. Introns can be positioned within the actual coding region of a gene or in the 5' and/or 3' untranslated region of a gene. Introns are contained within the mRNA precursor (unspliced mRNA). Each intron contains at least three highly conserved sequence elements essential for splicing: a 5' splice site, a branch point and a 3' splice site containing a run of pyrimidines called a polypyrimidine tract. The branch point or branch site is usually located approximately between 10 and 60 nucleotides upstream of the 3' splice site and forms during the splicing process via its conserved adenosine residue a lariat structure with the 5' splice site. The consensus sequence for the branch point is reported as YNYYRAY (with Y=T or C, R=A or G, N=any base; the conserved adenosine involved in the lariat formation is underlined) whereby in mammalians the preferred branch point sequence is TACTAAC (Zhuang et al., PNAS 86, 2752-2756, 1989). Often the branch point is adjacent to or within the polypyrimidine tract of the splice acceptor site.

"Splicing" or "spliced" refers to the mechanism by which a single functional RNA molecule is produced by the removal of one or more intron sequences during the processing of the primary transcript. Thereby splice donor sites interact with splice acceptor sites to allow splicing of the RNA or transcript and thus excision of the intron(s) bounded by the splice donor and acceptor sites. For each transcript the splice donor site splices with only ony splice acceptor site. In case of alternative splicing the splice donor site splices within the pools of transcripts with more than one splice acceptor site leading to a heterogeneous pool of transcripts. "Spliced mRNA" or "spliced transcript" refers herein to mRNA or transcripts produced by either removal of one or more intron sequences or by constructing a cDNA which when transcribed produces an mRNA or transcript having the same properties as an mRNA or transcript which had been subject to splicing but from which no nucleotide sequences had in fact been removed.

The term "splice site" refers to a specific sequence within a polynucleotide sequence that is present at either the 5' end or the 3' end of an intron. Recognition of these sites by the splicing machinery is followed by the excision of an intron or a polynucleotide sequence flanked by these sites. The term splice sites includes naturally occurring, engineered or synthetic, consensus or cryptic splice sites.

The terms "splice donor site", "5' splice site" or "SD" as used herein refer to a conserved sequence of a polynucleotide sequence surrounding the exon-intron boundary at the 5' end of an intron that marks the start of the intron and its boundary with the preceding exon sequence. The consensus sequence for a splice donor site consists of the sequence MAG:GTRAGT (with M=C or A, R=A or G and the colon denoting the site of exon-intron boundary=cleavage site) (Ohshima et al., J. Mol. Biol. 195, 247-259, 1987).

The terms "splice acceptor site", "3' splice site" or "SA" as used herein refer to a conserved sequence of a polynucleotiode sequence surrounding the intron-exon boundary at the 3' end of an intron that marks the end of the intron and its boundary with the following exon sequence. The consensus sequence for a splice acceptor site consists of the sequence $Y_{11-40}NYAG:R$ (SEQ ID NO: 21) (with Y=pyrimidine C or T, R=A or G, N=any base and the colon denoting the site of intron-exon boundary=cleavage site) (Ohshima et al., J. Mol. Biol. 195, 247-259, 1987).

Splice donor and splice acceptor sites are well known in the art and any may be utilized in the present invention. For a review see Ohshima et al., J. Mol. Biol. 195, 247-259, 1987. These elements can be found, inter alia, in the art or derived from consensus sequences, either empirically by inserting, deleting or substituting nucleotides, or by using software capable of predicting splicing sequences. One preferred splice donor and splice acceptor site in this invention is the consensus splice donor and splice acceptor site mentioned above. However, other sequences with sufficient splicing efficiency can be used as well. Efficient splice donor and acceptor sites suitable for this invention can be readily determined using techniques for measuring the efficiency of splicing. Intron splicing efficiency is readily determined by quantifying the spliced transcripts versus the full-length, unspliced transcripts that contain the intron(s), using methods known in the art such as quantitative PCR or Northern blot analysis, using appropriate probes for the transcripts. Reverse transcription-polymerase chain reaction (RT-PCR) can be used to analyze RNA samples containing mixtures of spliced and unspliced mRNA transcripts. For example, fluorescent-tagged primers annealing to polynucleotide sequences flanking the intron region are used to amplify both spliced and unspliced target sequences of the transcript. The resultant amplification products are then separated by gel electrophoresis and quantitated by measuring the fluorescent emission of the appropriate band(s). Alternatively, a quantitative PCR approach can be used to quantitate the different amplification products. A comparison is made to determine the amount of spliced and unspliced transcripts present in the RNA sample. Suitable splice donor and splice acceptor sites leading to correctly and efficiently spliced transcripts and thus to polypeptides of the expected sequence only at high level may also be determined by more indirect means by assessing product purity and heterogeneity, e.g. by Western Blot analysis or mass spectroscopy methods (e.g. MS, ESI, MALDI, LC/MS).

An "artificial intron", "non-native intron", "non-natural intron", "novel non-natural intron" or "novel non-native intron" according to the invention is an intron placed at the sequence position of a native intron, meaning identical to the intron position(s) in the native eukaryotic gene, but having a sequence different from the sequence of the native intron at this position. For example, an artificial intron derived from a non-immunoglobulin gene or derived from the constant region of a human kappa light chain gene is placed in an immunoglobulin signal peptide sequence within the codon encoding the amino acid at position −4 (counting backwards from the 3' end of the amino acid sequence of the signal peptide), within the codon encoding the first amino acid at position 118 in the constant domain CH1 of antibody heavy chains or within the codon encoding the first amino acid at position 231 in the constant domain CH2 of antibody heavy chains whereby in each case the placement is between the first and second nucleotide of the respective codon and thus corresponding to the positions of the native introns but the inserted intron sequence is not the native intron sequence. An artificial intron useful in the constructs of this invention will generally be an intron, which improves the expression of the gene of interest such as genes encoding for antibodies, enzymes, hormones, receptors, cytokines, lymphokines, adhesion molecules and derivatives or fragments thereof, when placed within the transcription unit compared to cells transfected with the same vectors but encoding the cDNA of this gene of interest with the coding sequence having the identical polynucleotide sequence (natural, modified, optimized, partially optimized or non-optimized) but without any intron within the transcription unit. Furthermore, an artificial intron useful in this invention will be an intron which leads to an at least comparable or improved expression of the gene of interest when placed in the transcription unit of this gene compared to cells transfected with the same vectors but encoding the genomic DNA of this gene of interest with the coding sequence having the identical polynucleotide sequence (natural, modified, optimized, partially optimized or non-optimized) and in which the natural intron(s) in the genomic DNA are in their natural sequence positions. The genomic DNA(s) to which the construct of the invention is compared to might thereby contain introns in one, two, more or all of their native positions normally also found in the natural or part of the natural gene(s). More than one artificial intron can be placed into positions of native introns of a transcription unit of a native eukaryotic gene which might still contain native introns in one, two, more or all of their native positions normally also found in the natural or part of the natural gene whereby either identical artificial introns or different artificial introns can be used. For expression of heteromeric proteins either identical or different introns can be placed into one, two or more native intron positions within the transcription units of the genes encoding the different polypeptides of a protein. Alternatively, an intron or several introns can be placed in just one or a few transcription units of the genes or all but one of the genes encoding the different polypeptides of a protein. Most preferred is the use of a single artificial intron within a gene to reduce the risk of alternative splicing and to reduce the size of the polynucleotide sequence.

The artificial intron can be a) derived from a natural intron from the gene of interest itself but modified by nucleotide substitutions, deletions and/or insertions, c) a natural intron from a different gene, d) derived from the natural intron from a different gene but modified by nucleotide substitutions, deletions and/or insertions, e) a chimeric intron composed of different intron sequences derived from one or more natural intron sequences of the gene of interest and/or of different genes, f) a de novo designed synthetic intron or g) any combination of the above.

Again, an intron becomes an artificial intron by virtue of its introduction at a sequence position of a native intron, meaning identical to the intron position(s) in the native eukaryotic gene, but having a sequence different from the sequence of the native intron at this position.

An intron useful in the constructs of this invention will generally be an efficient intron characterized by a splicing efficiency which results in all of the transcripts diverted to expression of the desired product. The efficient intron preferably has a splicing efficiency of about 90%-99%, preferably about 95-99%. Intron splicing efficiency is readily determined by quantifying the spliced transcripts versus the full-length, unspliced transcripts that contain the intron(s), using methods known in the art as described above.

Preferably, the artificial intron present in the constructs of the invention has efficient splice donor and acceptor sites, as defined above, such that splicing of the primary transcript occurs at a frequency greater than 90%, preferably at least 95% and even more preferred at least 99%. In this manner, at least 99% of the transcripts will be translated into desired product.

Preferably, an artificial intron present in the constructs of the invention has stop codons in all possible 3 reading frames and/or has a nucleotide sequence length which is not dividable by 3 to prevent a complete readthrough of the intron sequence in case of a non-splicing event. Furthermore, the intron contains a conserved branch site in the 3' region of the intron to allow for more efficient splicing. Ideally the intron sequence contains also a single restriction site close to the 5' end and/or the 3' end of the intron for subcloning purposes.

One intron suitable for use in the present invention is the intron from the human kappa light chain gene. In one embodiment, the intron from the human kappa light chain gene is further modified to introduce a) a single BglII restriction site close to the 5' end of the intron for cloning purposes, b) sequences which can act as stop codons in case of a non-splicing event of the messenger RNA which would then lead to premature translation termination of the protein and c) a conserved branch site in the 3' region of the intron to allow for more efficient splicing (SEQ ID NO: 1). In another embodiment, the intron used is the native intron from the hamster dihydrofolate reductase gene (SEQ ID NO:2). In a further embodiment, the intron used is an intron from the hamster dihydrofolate reductase gene further modified to introduce a single BglII restriction site close to the 5' end of the intron for cloning purposes and optimized splice donor and acceptor sequences (SEQ ID NO:3). The intron is inserted within the genes of interest using any of the various known methods for modifying a nucleic acid in vitro or as described in example 1. More than one intron, either identical or different ones, can be inserted within a gene of interest. If convenient restriction sites are lacking within the genes of interest, they can be introduced using linkers and oligonucleotides by PCR, ligation or restriction and annealing. Alternatively, the artificial intron-containing gene sequences can be prepared synthetically using various methods in organic chemistry.

A preferred intron is the nucleotide sequence comprising the sequence of SEQ ID NO:1, SEQ ID NO: 2 or SEQ ID NO:3 or modifications thereof which improve the expression of the gene of interest when placed within the transcription unit compared to cells transfected with the same vectors but encoding the cDNA of this gene of interest with the coding sequence having the identical polynucleotide sequence (native, modified, optimized, partially optimized or non-optimized) but without any intron within the transcription unit. Or the above introns lead as single intron to an at least comparable or even more preferred an improved expression of the gene of interest when placed in a position of a native intron of the transcription unit of this gene compared to cells transfected with the same vectors but encoding the genomic DNA of this gene of interest with the coding sequence having the identical polynucleotide sequence (native, modified, optimized, partially optimized or non-optimized) and in which the native intron(s) in the genomic DNA are in their natural sequence positions. The genomic DNAs to which the construct of the invention is compared to might thereby contain native introns in one, two, more or all positions normally also found in the native gene. Or the above artificial introns lead to an improved expression of the gene of interest when placed in a position of a native intron of the transcription unit of this gene in addition to the native introns in one, two, more or all positions normally also found in the native gene.

In a "comparative assay" the (artificial) intron to be tested is introduced in the transcription unit of the gene(s) of interest. The transcription units are cloned into expression vectors. These recombinant expression vectors are subsequently introduced into the test cells, e.g. CHO-DG44, by transfection and the influence of the (artificial) intron in question on the expression level of the gene of interest is determined for example by measuring the protein content of the gene of interest. Expression is compared to cells transfected with the same vectors but encoding either the cDNA of the corresponding gene(s) of interest with the coding sequence having the identical polynucleotide sequence (natural, modified, optimized, partially optimized or non-optimized) but without any intron within the transcription unit or the corresponding genomic DNA of this gene(s) of interest with the coding sequence having the identical polynucleotide sequence (native, modified, optimized, partially optimized or non-optimized) and in which native intron(s) in the genomic DNA are in one, two, more or all of their native sequence positions. A corresponding test is described in example 2 of the present invention.

For positioning of an intron within the position of a native intron of a transcription unit the nucleotide sequence successions shown in Table 1 encoding the indicated amino acids are preferred. If in the native polynucleotide sequence the amino acid pairs are not encoded by the preferred nucleotide successions the necessary adjustments in the nucleotide sequence can be achieved for example by performing site-specific mutagenesis, polymerase chain reaction mediated mutagenesis or de novo synthesis. Preferred are the nucleotide successions CAG:C, CAG:T, AAG:C, AAG:T, TAG:T or TAG:C whereby the colon denotes the site of intron insertion and even more preferred CAG:C, CAG:T, AAG:C or AAG:T. However, other sequences with sufficient splicing efficiency can be used as well especially if the amino acid sequence encoded by the nucleotide sequences flanking the site of intron insertion does not allow for the introduction of a preferred nucleotide succession. Intron sequences can be placed within an amino acid encoding codon or between two amino acid encoding codons. In case of using just a single artificial intron in a transcription unit which does not contain any further introns, intron positions closer to the 5" end of a transcription unit are preferred over positions in the 3' end of a transcription unit. Removal of the first intron from an mRNA precursor has been found to be cap-dependent. These caps are added to the 5' ends of RNAs cotranscriptionally after the first few nucleotides have been synthesized. This is followed by cotranscriptional splicing of the first intron and the efficiency is higher if the first intron is not too far away from the cap. Therefore, for transcription units encoding secreted proteins the intron can be placed within the nucleotide sequence encoding a suitable N-terminal signal peptide. Alternatively, in a transcription unit encoding antibodies the introns are placed preferentially within the codons encoding the first amino acid of the CH1 domain of heavy chains or the CL domain of light chains. In a transcription unit encoding antibody-derived fragments such as an Fc fusion protein the artificial introns are placed preferentially within the N-terminally of the Fc part located gene sequences of the fusion partner or within the codons encoding the first amino acid of the CH2 domains derived from an antibody heavy chain. The artificial introns can also be placed in positions of native introns within the 5' or 3' untranslated region of a transcription unit, most preferably into the 5' untranslated region.

TABLE 1

Preferred sites for positioning of artificial intron

| CAG:C | CAG:T | AAG:C | AAG:T | TAG:C | TAG:T |
|---|---|---|---|---|---|
| GlnLeu CAGCTN | GlnPhe CAGTTY | LysLeu AAGCTN | LysPhe AAGTTY | PheSer TTTAGC | PheSer TTTAGT |
| GlnPro CAGCCN | GlnLeu CAGTTR | LysPro AAGCCN | LysLeu AAGTTR | SerSer TCTAGC | SerSer TCTAGT |
| GlnHis CAGCAY | GlnSer CAGTCN | LysHis AAGCAY | LysSer AAGTCN | TyrSer TATAGC | TyrSer TATAGT |
| GlnGln CAGCAR | GlnTyr CAGTAY | LysGln AAGCAR | LysTyr AAGTAY | CysSer TGTAGC | CysSer TGTAGT |
| GlnArg CAGCGN | GlnCys CAGTGY | LysArg AAGCGN | LysCys AAGTGY | LeuSer CTTAGC | LeuSer CTTAGT |
| SerAla TCAGCN | GlnTrp CAGTGG | GlnAla CAAGCN | LysTrp AAGTGG | ProSer CCTAGC | ProSer CCTAGT |
| ProAla CCAGCN | SerVal TCAGTN | LysAla AAAGCN | GlnVal CAAGTN | HisSer CATAGC | HisSer CATAGT |
| ThrAla ACAGCN | ProVal CCAGTN | GluAla GAAGCN | LysVal AAAGTN | ArgSer CGTAGC | ArgSer CGTAGT |
| AlaAla GCAGCN | ThrVal ACAGTN | LeuSer YTAAGC | GluVal GAAGTN | IleSer ATTAGC | IleSer ATTAGT |
| PheSer TTCAGC | AlaVal GCAGTN | SerSer TCAAGC | LeuSer YTAAGT | ThrSer ACTAGC | ThrSer ACTAGT |
| SerSer TCCAGC | PheSer TTCAGT | ProSer CCAAGC | SerSer TCAAGT | AsnSer AATAGC | AsnSer AATAGT |
| TyrSer TACAGC | SerSer TCCAGT | GlnSer CAAAGC | ProSer CCAAGT | SerSer AGTAGC | SerSer AGTAGT |
| CysSer TGCAGC | TyrSer TACAGT | ArgSer MGAAGC | GlnSer CAAAGT | ValSer GTTAGC | ValSer GTTAGT |
| LeuSer CTCAGC | CysSer TGCAGT | IleSer ATAAGC | ArgSer MGAAGT | AlaSer GCTAGC | AlaSer GCTAGT |
| ProSer CCCAGC | LeuSer CTCAGT | ThrSer ACAAGC | IleSer ATAAGT | AspSer GATAGC | AspSer GATAGT |
| HisSer CACAGC | ProSer CCCAGT | LysSer AAAAGC | ThrSer ACAAGT | GlySer GGTAGC | GlySer GGTAGT |
| ArgSer CGCAGC | HisSer CACAGT | ValSer GTAAGC | LysSer AAAAGT | LeuAla YTAGCN | LeuVal YTAGTN |
| IleSer ATCAGC | ArgSer CGCAGT | AlaSer GCAAGC | ValSer GTAAGT | IleAla ATAGCN | IleVal ATAGTN |
| ThrSer ACCAGC | IleSer ATCAGT | GluSer GAAAGC | AlaSer GCAAGT | ValAla GTAGCN | ValVal GTAGTN |
| AsnSer AACAGC | ThrSer ACCAGT | GlySer GGAAGC | GluSer GAAAGT | | |

TABLE 1-continued

Preferred sites for positioning of artificial intron

| CAG:C | CAG:T | AAG:C | AAG:T | TAG:C | TAG:T |
|-------|-------|-------|-------|-------|-------|
| SerSer AGCAGC | AsnSer AACAGT | | GlySer GGAAGT | | |
| ValSer GTCAGC | SerSer AGCAGT | | | | |
| AlaSer GCCAGC | ValSer GTCAGT | | | | |
| AspSer GACAGC | AlaSer GCCAGT | | | | |
| GlySer GGCAGC | AspSer GACAGT | | | | |
| | GlySer GGCAGT | | | | | colon: site of intron insertion, N = any base, Y = C or T, R = A or G, M = C or A The term "synthetic" used in connection with a polynucleotide sequence is a non-natural polynucleotide (or portion of a polynucleotide) that differs from a wildtype polynucleotide sequence. For example, a synthetic gene or intron (or portion of a gene or intron) may contain one or more nucleic acid sequences not contiguous in nature (chimeric sequences), and/or may encompass substitutions, insertions, and deletions and combinations thereof.

As used herein, the term "hybridizes under stringent conditions" describes conditions for hybridization and washing which are known to those skilled in the art. Generally, stringent conditions are selected to be about 5-10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium. Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to about 50 nucleotides) and at least about 60° C. for long probes (e.g. greater than about 50 nucleotides). Exemplary stringent conditions include hybridization at 60 to 65° C. in a hybridization buffer with 5×SSC and washing at 42° C. with 0.2×SSC/0.1% SDS. A positive hybridization signal is at least 2 times above background hybridization. The terms "homology", "homologous", "identity", "identical", "sequence identity" or "homologous sequence" are used interchangeably. Methods for calculating "homology" or "identity" are well known in the art. For sequence comparison typically one sequence acts as a reference sequence to which test sequences are compared. The sequences are aligned for maximal correspondence. Gaps can be introduced in either of the nucleic acid sequences in the comparison for optimal alignment. Percent identity between two sequences is a function of the number of identical positions shared by the sequences, taking into account the number of gaps and the length of each gap which need to be introduced for optimal alignment of the two sequences. The comparison of sequences and determination of percent identity between two sequences can be accomplished using mathematical algorithms. Default program parameters can be used or alternative parameters can be designated. The sequence comparison algorithm then calculates the percent identity for the test sequence(s) relative to the reference sequence, based on the designated or default program parameters. One example of an algorithm that is suitable for determining identity is the BLAST algorithm (Altschul et al., J. Mol. Biol. 215, 403-410, 1990; Gish et al., Nature Genetics 3, 266-272, 1993; Madden et al., Meth. Enzymol. 266, 131-141, 1996; Zhang et al., Genome Res. 7, 649-656, 1997; Altschul et al., Nucleic Acids Res. 25, 3389-3402, 1997). Other computerized implementations of alignment algorithms are GAP, PILEUP, BESTFIT, FASTA and TFASTA in the Wisconsin Genetics Software Package. However, percent identity can be also determined by manual alignment and visual inspection and calculation.

"Exons" are defined as expressed regions of an eukaryotic gene which remain after the removal of the (artificial) introns via splicing from the messenger RNA (mRNA) precursor in the mature mRNA. Most exons contain only coding sequences but some exons are non-coding or partially coding exons. Usually they are positioned at the 5' or 3' end of an mRNA and contain untranslated, non-coding regions which might for example contribute enhancer or stabilization domains to the final transcript, resulting in increased translation of protein.

The term "vector" or "expression vector" as used herein relates to naturally occurring or synthetically generated constructs for uptake, proliferation, expression or transmission of nucleic acids in a cell, e.g. plasmids, minicircles, phagemids, cosmids, artificial chromosomes/mini-chromosomes, bacteriophages, viruses such as baculovirus, retrovirus, adenovirus, adeno-associated virus, herpes simplex virus, bacteriophages. Vectors can either integrate into the genome of the host cell or remain as autonomously replicating construct within the host cell. Methods used to construct vectors are well known to a person skilled in the art and described in various publications. In particular techniques for constructing suitable vectors, including a description of the functional and regulatory components such as promoters, enhancers, termination and polyadenylation signals, selection markers, origins of replication, and splicing signals, are known to the person skilled in the art. The eukaryotic expression vectors will typically contain also prokaryotic sequences that facilitate the propagation of the vector in bacteria such as an origin of replication and antibiotic resistance genes for selection in bacteria which might be removed before transfection of eukaryotic cells. A variety of eukaryotic expression vectors, containing a cloning site into which a polynucleotide can be operably linked, are well known in the art and some are commercially available from companies such as Agilent Technologies, Santa Clara, Calif.; Invitrogen, Carlsbad, Calif.; Promega, Madison, Wis. or Invivogen, San Diego, Calif.

A preferred embodiment of the invention are vectors or polynucleotide sequences containing one or more transcription units encoding genes of interest which comprise at least one artificial intron within one transcription unit. Also preferred according to the invention are vectors or polynucleotide sequences comprising a signal peptide sequence comprising an artificial intron for improved expression and having suitable restriction sites within the 3' end of the intron sequence or within or after the 3' end of the signal peptide sequence to allow the cloning of the gene of interest via recognitions sequences for restriction endonuclease in frame with the signal peptide sequence thus building a functional transcription unit encoding the complete gene of interest. Furthermore, preferred according to the invention are vectors or polynucleotide sequences comprising an artificial intron comprising signal peptide sequence which is flanked at its 3' end by sequences coding for the first amino acids of the variable region of an antibody or antibody-derived heavy or light chain or the Fc fusion partner which have suitable restriction sites within or after their sequence followed by the constant domain of an antibody light chain, the constant domains of an antibody heavy chain or an Fc region which have suitable restriction sites within or upstream of their 5' sequences whereby the restriction sites allow the insertion of the variable regions or the Fc fusion partner in frame with the already vector encoded parts of the transcription unit thus building a functional transcription unit encoding the complete gene of interest. The aforementioned constant domains or Fc regions might be flanked on their 5' site by sequences coding for the final amino acids of the variable region of antibody or antibody-derived heavy or light chain, the Fc fusion partner, linker sequences or other polypeptide sequences. Also preferred according to the invention are vectors or polynucleotide sequences comprising a signal peptide sequence having suitable restriction sites within or after the 3' end of the signal peptide sequence followed by the constant domain of an antibody light chain, constant domains of an antibody heavy chain or an Fc region comprising at least one artificial intron and which have suitable restriction sites within or upstream of their 5' sequences or within the 5' end of the artificial intron sequence whereby the restriction sites allow the insertion of the variable regions or the Fc fusion partner in frame with the already vector encoded parts of the transcription unit thus building a functional transcription unit encoding the complete gene of interest. The aforementioned constant domains or Fc regions might be flanked on their 5' site by sequences coding for the final amino acids of the variable region of antibody or antibody-derived heavy or light chain, the Fc fusion partner, linker sequences or other polypeptide sequences. And the aforementioned signal peptide sequences might be flanked on their 3' end by sequences coding for the first amino acids of the variable region of an antibody or antibody-derived heavy or light chain or the Fc fusion partner which have suitable restriction sites within or after their sequence.

The term "promoter" denotes a polynucleotide sequence which allows and controls the transcription of the genes or sequences operably connected therewith. A promoter contains recognition sequences for binding RNA polymerase and the initiation site for transcription (transcription initiation site). In order to express a desired sequence in a certain cell type or a host cell a suitable functional promoter must be chosen. A large number of promoters, including constitutive, inducible and repressible promoters from a variety of different sources, are well known in the art (and identified in databases such as GenBank) and are available as separate elements or elements cloned within polynucleotide sequences from commercial (e.g. depositories such as ATCC as well as other commercial sources) or individual sources. In inducible promoters the activity of the promoter may be increased or reduced in response to a signal. For example, the tetracycline (tet) promoter containing the tetracycline operator sequence (tetO) can be induced by a tetracycline-regulated transactivator protein (tTA). Binding of the tTA to the tetO is inhibited in the presence of tet. Examples for other inducible promoters are jun, fos, metallothionein and heat shock promoters. Of the promoters which are particularly suitable for high expression in eukaryotes, there are for example the ubiquitin/S27a promoter of the hamster (WO 97/15664), SV 40 early promoter, adenovirus major late promoter, mouse metallothionein-I promoter, the long terminal repeat region of Rous Sarcoma Virus, the early promoter of human Cytomegalovirus (CMV). Examples of other heterologous mammalian promoters are the actin, immunoglobulin or heat shock promoter(s).

The aforementioned promoters are well known in the art. A corresponding heterologous promoter can be functionally connected to other regulatory sequences in order to increase/regulate the transcription activity in an expression cassette. For example, the promoter may be functionally linked to enhancer sequences in order to increase the transcriptional activity. For this, one or more enhancers and/or several copies of an enhancer sequence may be used, e.g. a CMV or SV40 enhancer. Accordingly, an expression vector according to the invention, in another embodiment, contains one or more enhancers/enhancer sequences, preferably a CMV or SV40 enhancer.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The term "transcription termination site" or "transcription termination element" refers to a nucleotide sequence normally represented at the 3' end of the gene of interest or of the stretch of sequences to be transcribed, that causes RNA polymerase to terminate transcription.

The "polyadenylation signal" or "polyA" is a signal sequence which causes cleavage at a specific site at the 3' end of the eukaryotic mRNA and post-transcriptional incorporation of a sequence of about 100-200 adenine nucleotides (SEQ ID NO: 22) (polyA tail) at the cleaved 3' end. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

A "transcription unit", "expression unit" or "expression cassette" defines a region within a vector, construct or polynucleotide sequence that contains one or more genes to be transcribed, wherein the genes contained within the segment are operably linked to each other. They are transcribed from a single promoter and transcription is terminated by at least one polyadenylation signal. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequence that are contained within the unit. And each transcription unit may contain the same or different regulatory elements. For example, each transcription unit may contain the same terminator. IRES element or introns may be used for the functional linking of the genes within a transcription unit. A vector or polynucleotide sequence may contain more than one transcription unit.

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

To produce a secreted polypeptide the gene of interest usually includes a "signal sequence" encoding a "leader" or "signal peptide" that directs the newly synthesized polypeptide to and through the ER membrane where the polypeptide can be routed for secretion. The leader or signal peptide is often but not universally at the amino terminus of a secreted protein and is cleaved off by signal peptidases after the protein crosses the ER membrane. Signal peptides may also be called targeting signals, signal sequences, transit peptides, or localization signals. Signal peptides show great variance in overall length (approximately 15-50 amino acids) and amino acid sequence. All contain a hydrophobic region preceded by a domain with basic amino acids and followed by a slightly polar C-terminal domain. The latter often contains helix breaking proline or glycine residues as well as uncharged residues in positions −3 and −1 that determine the site of cleavage. The gene sequence will generally, but not necessarily, contain its own signal peptide sequence. Where the native signal peptide sequence is absent, a heterologous signal peptide sequence can be fused to the selected sequence. Or the native signal peptide sequence can be replaced by a heterologous one. Numerous signal peptide sequences are known to the skilled artisan and deposited in sequence databanks such as GenBank and EMBL. Signal peptides can direct proteins also to other organelles such as the nucleus, mitochondrial matrix, chloroplast, apoplast and peroxisome.

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. encephalomyocarditis virus (EMCV), picornavirus (e.g. FMDV), polio virus (PV), or hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance.

The terms "gene", "gene of interest", "desired sequence", "polynucleotide of interest" or "desired gene" as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or a truncated gene, a fusion or tagged gene, and can be a cDNA, a genomic DNA, or a DNA fragment. It is generally understood that genomic DNA encoding for a polypeptide or RNA includes non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

"Open reading frame" or "ORF" refers to a length of nucleic acid sequence, either DNA, cDNA or RNA, that comprises a translation start signal or initiation codon, such as an ATG or AUG, and a termination codon and can be potentially translated into a polypeptide sequence.

Within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3' end of the coding sequence in a way that transcription proceeds through the coding sequence into the polyadenylation signal. Linking is accomplished by recombinant methods known in the art, e.g. using PCR methodology, by ligation at suitable restrictions sites or by annealing. Synthetic oligonucleotide linkers or adaptors can be used in accord with conventional practice if suitable restriction sites are not present.

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The term "encoding" or "coding" refers to the inherent property of specific sequences of nucleotides in a nucleic acid, such as a gene in chromosome or an mRNA, to serve as templates for in vitro or in vivo synthesis of other polymers and macromolecules in biological processes having a defined sequence of nucleotides (i.e. rRNA, tRNA, other RNA molecules) or amino acids and the biological properties resulting therefrom. Accordingly, a gene codes for a protein if the desired protein is produced in a cell or another biological system by transcription and subsequent translation of the mRNA whereby the boundaries of the coding sequence are determined by a start codon at the 5' (amino) terminus and a translation stop codon at the 3' (carboxyl) terminus Both the coding strand, the nucleotide sequence of which is identical to the mRNA sequence and is usually provided in sequence listings of databanks, e.g. EMBL or GenBank, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns. In the Sequence Listing the sequences are presented as DNA rather than RNA sequence. For example, when presented as DNA the start codon is presented as ATG rather than AUG.

The term "cDNA" in the context of this invention refers to deoxyribonucleic acids produced by reverse transcription and typically second-strand synthesis of mRNA or other RNA produced by a gene. It can also be generated by de novo synthesis. If double-stranded, a cDNA molecule has both a coding or sense and a non-coding or antisense strand.

"Chemically synthesized" or "de novo synthesized" as related to a DNA sequence, means that the component nucleotides were assembled in vitro. Manual chemical synthesis of DNA may be accomplished using well-established procedures, or automated chemical synthesis can be performed using one of a number of commercially available machines. Furthermore, if needed the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available. Furthermore, potential cryptic splice sites, direct repeats, secondary structure elements and other motifs interfering with expression can be removed and the GC content optimized to improve RNA stability.

The terms "restriction endonuclease" and "restriction enzyme" are used interchangeably and refer to an enzyme that binds and cuts within a specific nucleotide sequence within double stranded DNA.

"Polymerase chain reaction" or "PCR" is an in vitro method for enzymatically amplifying specific nucleic acid sequences. Generally, knowledge of the sequence from the ends of the region of interest or beyond is needed such that oligonucleotide primers can be designed. These primers will be fully or in part identical or similar in sequence to opposite strands on the template to be amplified. PCR involves a repetitive series of temperature cycles with each cycle comprising three stages: denaturation of the template nucleic acid to separate the strands of the target molecule, annealing of single stranded oligonucleotide primer(s) to the template nucleic acid, and extension of the annealed primer(s) by DNA polymerase.

The term "expression" as used herein refers to transcription and/or translation of a heterologous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, or by immunostaining of the protein followed by FACS analysis PCR.

The term "polypeptide" is used interchangeably with "amino acid residue sequence", "amino acid sequence" or the term "protein" and refers to polymers of amino acids of any length. These terms also include proteins that are post-translationally modified through reactions that include, but are not limited to glycosylation, glycation, acetylation, phosphorylation, oxidation, amidation or protein processing. Modifications and changes, for example fusions to other proteins, amino acid sequence substitutions, deletions or insertions, can be made in the structure of a polypeptide while the molecule maintains its biophysical properties and/or biological functional activity. For example certain amino acid sequence substitutions can be made in a polypeptide or its underlying nucleic acid coding sequence and a protein can be obtained with like properties. Furthermore, modifications and changes can be made in the structure of a polypeptide to gain or improve biophysical properties and/or to modulate, introduce or abrogate biological functional activity. For example, modification and changes can be introduced to improve the solubility and/or stability of a protein, such as introducing the amino substitution Ser228Pro in the hinge region of an IgG4 molecule to stabilize the intermolecular disulfide bridge between the heavy chains and thus reducing the occurrence of half molecules. Or in case of IgGs amino acid substitutions can be made to modulate binding to one or more Fc gamma receptors to either improve or abrogate antibody dependent cellular cytotoxicity, or to improve binding to the neonatal Fc receptor for prolonged half-life or to improve or abrogate binding to components involved in the complement dependent cytotoxicity. Amino acid modifications can be prepared for example by performing site-specific mutagenesis or polymerase chain reaction mediated mutagenesis on its underlying nucleic acid sequence. The term "polypeptide" thus also includes, for example, fusion proteins consisting of an immunoglobulin component, e.g. the Fc component, and a growth factor, e.g. an interleukin. In addition, the polypeptides may multimerise and form homo- or heteromers.

"Immunoglobulins", or "antibodies" are proteins selected from among the globulins, which are formed as a reaction of the host organism to a foreign substance (=antigen) from differentiated B-lymphocytes (plasma cells). They serve to defend specifically against these foreign substances. There are various classes of immunoglobulins: IgA, IgD, IgE, IgG, IgM, IgY, IgW.

The terms immunoglobulin and antibody are used interchangeably. As used herein, the term "immunoglobulin" or "antibody" includes a polyclonal, monoclonal, monospecific, bi-specific, multi-specific, a single chain antibody, an antigen-binding fragment of an antibody (e.g., an Fab or F(ab')$_2$ fragment), a disulfide-linked Fv, etc. Antibodies can be of any species and include chimeric and humanized antibodies. "Chimeric" antibodies are molecules in which antibody domains or regions are derived from different species. For example the variable region of heavy and light chain can be derived from rat or mouse antibody and the constant regions from a human antibody. In "humanized" antibodies only minimal sequences are derived from a non-human species. Often only the CDR amino acid residues of a human antibody are replaced with the CDR amino acid residues of a non-human species such as mouse, rat, rabbit or llama. Sometimes a few key framework amino acid residues with impact on antigen binding specificity and affinity are also replaced by non-human amino acid residues. Antibodies may be produced through chemical synthesis, via recombinant or transgenic means, via cell (e.g., hybridoma) culture, or by other means.

Immunoglobulins are tetrameric polypeptides composed of two pairs of a heterodimer each formed by a heavy and light chain. Stabilization of both the heterodimers as well as the tetrameric polypeptide structure occurs via interchain disulfide bridges. Each chain is composed of structural domains called "immunoglobulin domains" or "immunoglobulin regions" whereby the terms "domain" or "region" are used interchangeably. Each domain contains about 70-110 amino acids and forms a compact three-dimensional structure. Both heavy and light chain contain at their N-terminal end a "variable domain" or "variable region" with less conserved sequences which is responsible for antigen recognition and binding. The variable region of the light chain is also referred to as "VL" and the variable region of the heavy chain as "VH". The variable regions exhibit the same general structure of 4 relatively conserved framework regions, also referred to as "FR1" to "FR4", interspersed by three hypervariable regions, also called complementarity determining regions ("CDR"), which are the main contributors to the specific binding of an antigen. CDR and FR residues are determined according to the standard sequence definition (Kabat et al. (1991), "Sequences of proteins of immunological interest", US Dept. Health and Human Services) and a structural definition (Chothia and Les, J. Mol. Biol. 196, 901-917, 1987). The substructure of a VH or VL region can be described as follows: FR1-CDR1-FR2-CDR2-FR3-CDR3-FR4. The C-terminal part of each chain contains one or more domains with much more conserved "constant" sequences, also called "constant domains" or "constant regions". An immunoglobulin light chain, kappa or lambda type, contains a single constant domain, also referred to as "CL" domain or region. The constant domains of an immunoglobulin heavy chain are called "CH" domains or regions. Depending on the immunoglobulin class the number of domains varies between 3 and 4. The heavy chain of an IgG class immunoglobulin with the subclasses IgG1, IgG2, IgG3 and IgG4 contains 3 different CH domains: "CH1", "CH2" and "CH3". The immunoglobulin fragments composed of the CH2 and CH2 domains of the heavy chain are called "Fc fragments", "Fc region" or "Fc" because of their crystallization propensity (Fc=fragment crystallizable). Between CH1 and CH2 a region with more variation with regard to sequence and length between the different immunoglobulin classes and subclasses is found, the "hinge region" also referred to as "hinge" or "H". It not only stabilizes the heterodimers by interchain disulfide bridges between the heavy chains but it also determines the flexibility between both Fab arms and the flexibility between the Fab arms and the Fc region of the immunoglobulin molecule. The substructure of an IgG heavy chain can be described as follows: CH1-H—CH2-CH3.

The term "antibody derived molecules" is used interchangeably with "antibody derived fragments" or "antibody fragments" and refers to polypeptides which contain only part(s) of one or more antibody domain(s) or region(s) and/or complete domain(s) or region(s). The antibody fragments can be either a) forming a molecule on their own, b) linked with each other in different combinations, c) fused to non-antibody sequences, d) fused or linked to non-polypetide (e.g. radionucleotides) or d) any combination of the above. These polypeptides can exist either as monomers or as multimers whereby polypeptides can have identical or different sequences.

"Fab fragments" (Fragment antigen-binding=Fab) or "Fab" consist of the variable regions of both antibody heavy and light chains (VH and VL) which are held together by the adjacent constant regions (CH1 and CL). These may be formed by protease digestion, e.g. with papain, from conventional antibodies, but similar Fab fragments may also be produced in the mean time by genetic engineering. Further antibody fragments include "F(ab')2 fragments" or "F(ab') 2", which may be prepared by proteolytic cleaving with pepsin or by genetic engineering in which both Fab arms of an antibody are still linked via inter-heavy chain disulfide bridges located within the hinge region.

The immunoglobulin fragments composed of the CH2 and CH3 domains of the antibody heavy chain are called "Fc fragments", "Fc region" or "Fc" because of their crystallization propensity (Fc=fragment crystallizable). These may be formed by protease digestion, e.g. with papain or pepsin from conventional antibodies but may also be produced by genetic engineering. The N-terminal part of the Fc fragment might vary depending on how many amino acids of the hinge region are still present.

The term "Fc-fusion protein" describes polypeptides which contain as a fusion partner a natural or modified (e.g. substitutions, deletions, insertions) Fc region of an immunoglobulin. Fc fusion proteins can be either naturally occurring proteins (e.g. antibodies) or engineered recombinant proteins (e.g. TNF receptor-Fc fusion protein or a VH region fused to an Fc region). The Fc-fusion proteins can exist either as monomers or as multimers whereby polypeptides can have identical or different sequences, might contain linker sequences between the two fusion partners and/or part of the hinge region or modified hinge regions or the polypeptide is fused directly to the CH2 domain.

Using genetic engineering methods it is possible to produce shortened antibody fragments which consist only of the variable regions of the heavy (VH) and of the light chain (VL). These are referred to as "Fv fragments" (Fragment variable=fragment of the variable part) or "Fv". Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a "single-chain-Fv" or "scFv". Examples of scFv-antibody proteins of this kind are known from the prior art. In addition, more than one VH and/or VL region can be linked together. In addition, the polypeptides may multimerise and form homo- or heteromers.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the linker in an scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins are known from the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a linker region. Examples of minibody-antibody proteins are known from the prior art.

By triabody the skilled person means a: trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures. In a preferred embodiment of the present invention, the gene of interest is encoded for any of those desired polypeptides mentioned above, preferably for a monoclonal antibody, a derivative or fragment thereof.

The "polypeptide of interest", "protein of interest" or "product of interest" includes proteins, polypeptides, fragments thereof, peptides, fusion proteins all of which can be expressed in the selected host cell. Desired proteins can be for example antibodies, enzymes, cytokines, lymphokines, adhesion molecules, receptors and derivatives or fragments thereof, and any other polypeptides that can serve as agonists or antagonists and/or have therapeutic or diagnostic use. Other proteins of interest are, for example, proteins/polypeptides, which are used to change the properties of host cells within the scope of so-called "Cell Engineering", such as e.g. anti-apoptotic proteins, chaperones, metabolic enzymes, glycosylation enzymes and the derivatives or fragments thereof, but are not restricted thereto.

Especially, desired proteins/polypeptides or proteins of interest are for example, but not limited to Fc receptors, enzymes, tumor necrosis factor receptor, growth hormone receptors, insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1, VEGF and nanobodies. Also included is the production of erythropoietin or any other hormone growth factors and any other polypeptides that can serve as agonists or antagonists and/or have therapeutic or diagnostic use. The method according to the invention can also be advantageously used for production of antibodies, such as monoclonal, polyclonal, multispecific and single chain antibodies, or fragments derived thereof, e.g. Fab, Fab', F(ab')2, Fc and Fc'-fragments, heavy and light immunoglobulin chains and their constant, variable or hypervariable region as well as Fv- and Fd-fragments.

The "product of interest" may also be an antisense RNA, tRNA, rRNAs, other RNAs being part of riboproteins or other regulatory RNAs.

The method of the present invention may be performed in all eukaryotic cells. Cells and cell lines may be present e.g. in a cell culture and include but are not limited to eukaryotic cells, such as yeast, plant, insect or mammalian cells. For example, the cells may be oocytes, embryonic stem cells, hematopoietic stem cells or any type of differentiated cells. A method is preferred wherein the eukaryotic cell is a mammalian cell. More preferred is a method wherein the mammalian cell is a rodent cell. Furthermore, preferred is a method wherein the mammalian cell is a human, simian, murine, rat, rabbit, hamster, goat, bovine, sheep or pig cell. Preferred cell lines or "host cells" for the production of biopharmaceuticals are human, mice, rat, monkey, or rodent cell lines. More preferred are hamster cells, preferably BHK21, BHK TK⁻, CHO, CHO-K1, CHO-DUKX, CHO-DUKX B 1, CHO-S and CHO-DG44 cells or the derivatives/progenies of any of such cell lines. Particularly preferred are CHO-DG44, CHO-DUKX, CHO-K1, CHO-S and BHK21, and even more preferred CHO-DG44 and CHO-DUKX cells. Furthermore, murine myeloma cells, preferably NS0 and Sp2/0 cells or the derivatives/progenies of any of such cell lines are also known as production cell lines for biopharmaceutical proteins.

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-SFMII (Invitrogen), serum-free CHO Medium (Sigma), protein-free CHO Medium (Sigma), EX-CELL® Media (SAFC), Hyclone™ CDM4CHO™ and Hyclone™ SFM4CHO™ are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing a selectable gene a suitable selection agent can be added to the culture medium.

The "transfection" of eukaryotic host cells with polynucleotide sequences or expression vectors, resulting in genetically modified cells, recombinant or transgenic cells, can be performed by any method well known to the skilled artisan. Transfection methods include but are not limited to liposome-mediated transfection, calcium phosphate co-precipitation, electroporation, polycation (e.g. DEAE dextran)-mediated transfection, protoplast fusion, microinjection and viral infections. Preferably, the transfection is a stable transfection. The transfection method that provides optimal transfection frequency and expression of the heterologous genes or polynucleotides in the particular host cell line and type is favored. Suitable methods can be determined by routine procedures. For stable transfectants the constructs are either integrated into the host cell's genome or an artificial chromosome/mini-chromosome or located episomally so as to be stably maintained within the host cell. For generation of genetically modified cells expressing the product(s) of interest all required heterologous genes can be located on a single vector or polynucleotide sequence in mono- or multicistronic transcription units. In this case the host cell is transfected with single vectors or polynucleotide sequences. The heterologous genes can also be positioned on different vectors or polynucleotide sequences. In this case host cells are either co-transfected with all vectors or polynucleotide sequences and/or are transfected in successive rounds with the vectors or polynucleotide sequences encoding the genes of interest. In case of co-transfection the ratios of the different vectors can be varied.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, a hamster actin gene introduced into a hamster host cell is by definition a heterologous gene. The term "recombinant" is used exchangeably with the term "heterologous" throughout the specification of this present invention, especially in the context with protein expression. Thus, a "recombinant" protein is a protein expressed from a heterologous or recombinant polynucleotide sequence.

The term "selection marker gene" refers to a gene that only allows cells carrying the gene to be specifically selected for or against in the presence of a corresponding selection agent. By way of illustration, an antibiotic resistance gene can be used as a positive selectable marker gene that allows the host cell transformed with the gene to be positively selected for in the presence of the corresponding antibiotic; a non-transformed host cell would not be capable of growth or survival under the selection culture conditions. Selectable markers can be positive, negative or bifunctional. Positive selectable markers allow selection for cells carrying the marker by conferring resistance to a drug or compensate for a metabolic or catabolic defect in the host cell. In contrast, negative selection markers allow cells carrying the marker to be selectively eliminated. For example, using the HSV-tk gene as a marker will make the cells sensitive to agents such as acyclovir and gancyclovir. The selectable marker genes used herein, including the amplifiable selectable genes, will include recombinantly engineered mutants and variants, fragments, functional equivalents, derivatives, homologs and fusions of the native selectable marker gene so long as the encoded product retains the selectable property. Useful derivatives generally have substantial sequence similarity (at the amino acid level) in regions or domains of the selectable marker associated with the selectable property. A variety of marker genes, well known to the skilled artisan, have been described, including bifunctional (i.e. positive/negative) markers (see e.g. WO 92/08796 and WO 94/28143), incorporated by reference herein. For example, selectable genes commonly used with eukaryotic cells include the genes for aminoglycoside phosphotransferase (APH), hygromycin phosphotransferase (HYG), dihydrofolate reductase (DHFR), thymidine kinase (TK), glutamine synthetase, asparagine synthetase, and genes encoding resistance to neomycin (G418), puromycin, histidinol D, bleomycin and phleomycin.

The "selectable amplifiable marker gene" usually encodes an enzyme which is required for growth of eukaryotic cells under those conditions. For example, the selectable amplifiable marker gene may encode DHFR which gene is amplified when a host cell transfected therewith is grown in the presence of the selective agent, methotrexate (MTX). Accordingly, host cells genetically modified according to any method described herein are encompassed by this invention, wherein the selectable amplifiable marker gene encodes for example for a polypeptide having the function of dihydrofolate reductase (DHFR), glutamine synthetase, CAD, adenosine deaminase, adenylate deaminase, UMP synthetase, IMP 5'-dehydrogenase, xanthine guanine phosphoribosyl transferase, HGPRTase, thymidine kinase, thymidylate synthetase, P glycoprotein 170, ribonucleotide reductase, asparagine synthetase, arginosuccinate synthetase, ornithine decarboxylase, HMG CoA reductase, acetylglucosaminyl transferase, threonyl-tRNA synthetase or Na$^+$K$^+$-ATPase. For a review of the exemplary selectable amplifiable marker genes see Kaufman, Methods in Enzymology, 185, 537-566, 1990.

One particular selectable amplifiable marker gene is the gene encoding dihydrofolate reductase (DHFR) which is necessary for the biosynthesis of purines. Cells lacking the DHFR gene will not grow on medium lacking purines. The DHFR gene is therefore useful as a dominant selectable marker to select and amplify genes in such cells growing in medium lacking purines. The selection agent used in conjunction with a DHFR gene is methotrexate (MTX).

Another selection and/or amplification marker is the glutamine synthetase (GS) gene. The GS gene encodes the glutamine synthetase enzyme which is required for synthesis of the amino acid glutamine Cells lacking the GS gene or expressing low endogenous GS levels will not grow in glutamine-free media. The GS gene is therefore useful as a dominant selectable marker to select and amplify genes in such cells growing in glutamine-free medium. The selection agent used in conjunction with the GS gene is methionine sulfoximine (MSX).

Selection may also be made by fluorescence activated cell sorting (FACS) using for example a cell surface marker, bacterial beta-galactosidase or fluorescent proteins (e.g. green fluorescent proteins (GFP) and their variants from *Aequorea victoria* and *Renilla reniformis* or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" refers to a substance that interferes with the growth or survival of a host cell that is deficient in a particular selectable gene. For example, to select for the presence of an antibiotic resistance gene like APH (aminoglycoside phosphotransferase) in a transfected cell the antibiotic Geneticin (G418) is used. The selection agent can also comprise an "amplifying agent" which is defined for purposes herein as an agent for amplifying copies of the amplifiable gene if the selectable marker gene relied on is an amplifiable selectable marker. For example, methotrexate is a selection agent useful for the amplification of the DHFR gene.

The term "gene expression" or "expression" relates to the transcription and/or translation of a heterologous gene sequence in a host cell. The expression rate can be generally determined, either on the basis of the quantity of corresponding mRNA which is present in the host cell or on the basis of the quantity of gene product produced which is encoded by the gene of interest. The quantity of mRNA produced by transcription of a selected nucleotide sequence can be determined for example by Northern blot hybridisation, ribonuclease-RNA-protection, in situ hybridisation of cellular RNA or by PCR methods (e.g. quantitative PCR). Proteins which are encoded by a selected nucleotide sequence can also be determined by various methods such as, for example, ELISA, protein A HPLC, western blot, radioimmunoassay, immunoprecipitation, detection of the biological activity of the protein, immune staining of the protein followed by FACS analysis or fluorescence microscopy, direct detection of a fluorescent protein by FACS analysis or fluorescence microscopy or by spectrophotometry.

By "increased titer or productivity", "increased expression" or "improved expression or productivity" is meant the increase in expression, synthesis or secretion of a heterologous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably—two-fold to five-fold particularly preferably a three-fold to five-fold increase in specific productivity or titer.

An increased titer, productivity or expression may be obtained by using one of the artificial intron-containing gene set-ups according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

The term "titer" is a statement of the product concentration in a defined volume, e.g. ng/mL, mg/mL, mg/L, g/L.

The term "specific productivity" refers to the amount of protein produced by the cell, in pg per cell and per day. It is calculated using the formula $pg/((C_t-C_0)t/\ln(C_t-C_0))$, where $C_0$ and $C_t$ indicate the number of cells on seeding or harvesting and t is the cultivation period.

A further embodiment of the above mentioned methods relates to a method, wherein the polypeptide(s)/product(s) which is/are encoded by the gene(s) of interest and being expressed in said host cell, is/are isolated from the cells or the cell culture supernatant, if secreted into the culture medium.

Said production cells are cultivated preferentially in serum-free medium and in suspension culture under conditions which are favorable for the expression of the desired gene(s) and isolating the protein of interest from the cells and/or the cell culture supernatant. Preferably the protein of interest is recovered from the culture medium as a secreted polypeptide, or it can be recovered from host cell lysates if expressed without a secretory signal. It is necessary to purify the protein of interest from other recombinant proteins, host cell proteins and contaminants in a way that substantially homogenous preparations of the protein of interest are obtained. As a first step often cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE. In general, methods teaching a skilled person how to purify a heterologous protein expressed by host cells, are well known in the art.

The practice of the present invention will employ, unless otherwise indicated, conventional techniques of cell biology, molecular biology, cell culture, immunology and the like which are in the skill of one in the art. These techniques are fully disclosed in the current literature.

The invention concerns a transcription unit or expression vector comprising a gene of interest and comprising at least one artificial intron, whereby the artificial intron is
i. replacing a native intron sequence within said gene of interest, or
ii. positioned at the site of a native intron position within said gene of interest.

In a preferred embodiment the at least one artificial intron replaces a native intron sequence within said gene of interest.

In a specific embodiment the artificial intron sequence comprises a nucleotide sequence at least 75%, 80%, 85%, 90%, 95%, 99%, 100% identical to SEQ ID NO: 1, SEQ ID NO: 2 or SEQ ID NO:3.

In a further specific embodiment the artificial intron sequence is SEQ ID NO: 1, SEQ ID NO: 2 or SEQ ID NO:3, preferably the artificial intron sequence is SEQ ID NO: 1 or SEQ ID NO: 3.

The novel introns are designed to have additional functionality and/or greater efficacy than unmodified introns, e.g. they comprise sequences which can act as stop codons in case of a non-splicing event of the messenger RNA leading to premature translation termination of the protein or have optimized splice donor and acceptor sequences included. Additionally, the novel introns of the present invention lead to an at least comparable or preferably improved expression of a gene of interest, especially genes encoding antibodies and antibody derived fragments.

In another embodiment said artificial intron is operably linked to a heterologous coding sequence of a gene.

In a preferred embodiment the gene of interest is an immunoglobulin gene, preferably said immunoglobulin gene encodes an IgG1, IgG2, or IgG4.

In a further embodiment the gene of interest encodes at least one domain of an immunoglobulin gene, preferably an Fc fusion protein, or a single chain format or another antibody-derived molecule. Preferably said domain is a variable domain.

In another specific embodiment the domain of an immunoglobulin gene is the variable domain of the heavy chain (VH) or the variable domain of the light chain (VL).

In a further embodiment said domain is a constant domain of an immunoglobulin gene or a hinge region of an immunoglobulin gene. Preferably the constant domain of an immunoglobulin gene is a CH1, a CH2 or a CH3 domain of the heavy chain or a CL domain of the light chain.

In another embodiment of the present invention relating to the domain of an immunoglobulin the artificial intron is located within the codon encoding the first amino acid at position 108 in the constant domain CL of immunoglobulin kappa and lambda light chains between the first and second nucleotide of the codon, within the codon encoding the first amino acid at position 118 in the constant domain CH1 of immunoglobulin heavy chains between the first and second nucleotide of the codon, within the codon encoding the first amino acid at position 216 in the hinge region of immunoglobulin heavy chains between the first and second nucleotide of the codon, within the codon encoding the first amino acid at position 231 in the constant domain CH2 of immunoglobulin heavy chains between the first and second nucleotide of the codon and/or within the codon encoding the first amino acid at position 341 in the constant domain CH3 of immunoglobulin heavy chains between the first and second nucleotide of the codon.

In a further embodiment of the present invention the gene of interest is an Fc-fusion protein.

In another specific embodiment of the present invention said gene/sequence contains at least one amino acid substitution/mutation modulating the biological (such as ADCC, half life, binding etc.) and/or biophysical properties (such as stability, solubility etc.) of the encoded protein within a immunoglobulin domain. Preferably said gene/sequence is a VH, VL, CH1, CH2, CH3, or hinge region.

In a specific embodiment of the present invention relating to an Fc-fusion protein the artificial intron is located within the codon encoding the first amino acid at position 216 in the hinge region of an immunoglobulin heavy chain between the first and second nucleotide of the codon if part of the Fc-fusion protein, within the codon encoding the first amino acid at position 231 in the constant domain CH2 of an immunoglobulin heavy chain between the first and second nucleotide of the codon and/or within the codon encoding the first amino acid at position 341 in the constant domain CH3 of an immunoglobulin heavy chain between the first and second nucleotide of the codon.

In a further embodiment of the present invention the artificial intron is positioned in a signal peptide sequence operably linked to a heterologous coding sequence of a gene. Preferably the signal peptide is a signal peptide of an immunoglobulin gene.

In a specific embodiment of the present invention relating to a signal peptide sequence the artificial intron is located within the codon encoding the amino acid at position −4 (counting backwards from the 3' end of the amino acid sequence of the signal peptide) of the signal peptide sequence of immunoglobulin heavy and/or light chains between the first and second nucleotide of the codon.

In a further embodiment of the present invention the expression of the gene of interest is increased compared to a control transcription unit or control expression vector which does not comprise an artificial intron, preferably the expression is increased at least 20%.

In yet another embodiment of the present invention the artificial intron is positioned within the nucleotide sequence successions CAG:C, CAG:T, AAG:C, AAG:T, TAG:T or TAG:C, preferably CAG:C, CAG:T, AAG:C or AAG:T, whereby the colons denote the site of intron insertion, and one of the following amino acid pairs is encoded at the intron insertion site:

| CAG:C | CAG:T | AAG:C | AAG:T | TAG:C | TAG:T |
|---|---|---|---|---|---|
| GlnLeu CAGCTN | GlnPhe CAGTTY | LysLeu AAGCTN | LysPhe AAGTTY | PheSer TTTAGC | PheSer TTTAGT |
| GlnPro CAGCCN | GlnLeu CAGTTR | LysPro AAGCCN | LysLeu AAGTTR | SerSer TCTAGC | SerSer TCTAGT |
| GlnHis CAGCAY | GlnSer CAGTCN | LysHis AAGCAY | LysSer AAGTCN | TyrSer TATAGC | TyrSer TATAGT |
| GlnGln CAGCAR | GlnTyr CAGTAY | LysGln AAGCAR | LysTyr AAGTAY | CysSer TGTAGC | CysSer TGTAGT |
| GlnArg CAGCGN | GlnCys CAGTGY | LysArg AAGCGN | LysCys AAGTGY | LeuSer CTTAGC | LeuSer CTTAGT |
| SerAla TCAGCN | GlnTrp CAGTGG | GlnAla CAAGCN | LysTrp AAGTGG | ProSer CCTAGC | ProSer CCTAGT |
| ProAla CCAGCN | SerVal TCAGTN | LysAla AAAGCN | GlnVal CAAGTN | HisSer CATAGC | HisSer CATAGT |

-continued

| CAG:C | CAG:T | AAG:C | AAG:T | TAG:C | TAG:T |
|---|---|---|---|---|---|
| ThrAla ACAGCN | ProVal CCAGTN | GluAla GAAGCN | LysVal AAAGTN | ArgSer CGTAGC | ArgSer CGTAGT |
| AlaAla GCAGCN | ThrVal ACAGTN | LeuSer YTAAGC | GluVal GAAGTN | IleSer ATTAGC | IleSer ATTAGT |
| PheSer TTCAGC | AlaVal GCAGTN | SerSer TCAAGC | LeuSer YTAAGT | ThrSer ACTAGC | ThrSer ACTAGT |
| SerSer TCCAGC | PheSer TTCAGT | ProSer CCAAGC | SerSer TCAAGT | AsnSer AATAGC | AsnSer AATAGT |
| TyrSer TACAGC | SerSer TCCAGT | GlnSer CAAAGC | ProSer CCAAGT | SerSer AGTAGC | SerSer AGTAGT |
| CysSer TGCAGC | TyrSer TACAGT | ArgSer MGAAGC | GlnSer CAAAGT | ValSer GTTAGC | ValSer GTTAGT |
| LeuSer CTCAGC | CysSer TGCAGT | IleSer ATAAGC | ArgSer MGAAGT | AlaSer GCTAGC | AlaSer GCTAGT |
| ProSer CCCAGC | LeuSer CTCAGT | ThrSer ACAAGC | IleSer ATAAGT | AspSer GATAGC | AspSer GATAGT |
| HisSer CACAGC | ProSer CCCAGT | LysSer AAAAGC | ThrSer ACAAGT | GlySer GGTAGC | GlySer GGTAGT |
| ArgSer CGCAGC | HisSer CACAGT | ValSer GTAAGC | LysSer AAAAGT | LeuAla YTAGCN | LeuVal YTAGTN |
| IleSer ATCAGC | ArgSer CGCAGT | AlaSer GCAAGC | ValSer GTAAGT | IleAla ATAGCN | IleVal ATAGTN |
| ThrSer ACCAGC | IleSer ATCAGT | GluSer GAAAGC | AlaSer GCAAGT | ValAla GTAGCN | ValVal GTAGTN |
| AsnSer AACAGC | ThrSer ACCAGT | GlySer GGAAGC | GluSer GAAAGT | | |
| SerSer AGCAGC | AsnSer AACAGT | | GlySer GGAAGT | | |
| ValSer GTCAGC | SerSer AGCAGT | | | | |
| AlaSer GCCAGC | ValSer GTCAGT | | | | |
| AspSer GACAGC | AlaSer GCCAGT | | | | |
| GlySer GGCAGC | AspSer GACAGT | | | | |
| | GlySer GGCAGT | | | | | colon: site of intron insertion, N = any base, Y = C or T, R = A or G, M = C or A Preferably said transcription unit or expression vector further comprises at least one promoter and at least one terminator, optionally said transcription unit or expression vector further comprises at least one selection marker (bacterial or eukaryotic) and/or at least one enhancer.

In a preferred embodiment said promoter is a CMV promoter, ubiqutin promoter, elongation factor promoter. Said selection marker is preferably an amplifiable selection marker like dihydrofolate reductase or glutamine synthetase and/or a non-amplifiable selection marker like neomycin, puromycin, hygromycin, or ampicillin resistance marker. Said terminator is preferably a polyadenylation sequence from hamster growth hormone, SV40 or bovine growth hormone. Said enhancer is preferably from CMV or SV40.

The invention further concerns a host cell comprising the transcription unit or expression vector of the present invention. Preferably said cell is a eukaryotic cell, more preferably a mammalian cell, most preferably a rodent cell. In a specifically preferred embodiment said cell is a hamster cell like Chinese hamster ovary (CHO) cell. In a further preferred embodiment said CHO cell is CHO DG44, CHO DUKX.

The invention further concerns the use of the transcription unit or the expression vector according to any one of the above embodiments of the present invention for improving the productivity of a cell.

The invention further concerns a method of producing a heterologous protein of interest, encoded by a polynucleotide sequence, whereby said method comprises the following steps:
a) introducing at least one artificial intron sequence into said polynucleotide sequence by
  i. replacing a native intron sequence within said polynucleotide sequence, or
  ii. by introducing at least one artificial intron sequence at the site of a native intron position, and
b) introducing the polynucleotide sequence of step a) comprising the artificial intron sequence into a transcription unit or an (mammalian) expression vector, and
c) transfecting a cell with said transcription unit or said vector of step b), and
d) cultivating said cell of step c) under conditions which allow expression of said protein of interest.

The invention further concerns a method of producing a heterologous protein of interest, encoded by a polynucleotide sequence, whereby said method comprises the following steps:
a) introducing at least one artificial intron sequence into a transcription unit or an (mammalian) expression vector comprising a polynucleotide sequence encoding the protein of interest by
  i. replacing a native intron sequence within said polynucleotide sequence or
  ii. by introducing at least one artificial intron sequence at the site of a native intron position, and
b) transfecting a cell with said transcription unit or (mammalian) expression vector of step a), and
c) cultivating said cell of step b) under conditions which allow expression of said protein of interest.

The invention further concerns a method of producing a protein of interest encoded by a polynucleotide sequence, whereby said method comprises the following steps:
a) transfecting a (mammalian) cell with the transcription unit or expression vector of the present invention,
b) cultivating said cell of step a) under conditions which allow expression of said protein of interest.

In a specific embodiment of the methods of the present invention the protein of interest is an immunoglobulin or antibody-derived fragment.

In another specific embodiment of the methods of the present invention the artificial intron sequence is at least 75%, 80%, 85%, 90%, 95%, 99%, 100% identical to SEQ ID NO: 1, SEQ ID NO: 2 or SEQ ID NO:3.

In a further embodiment of the methods of the present invention the artificial intron sequence is SEQ ID NO: 1, SEQ ID NO: 2 or SEQ ID NO:3, preferably the artificial intron sequence is SEQ ID NO: 1 or SEQ ID NO: 3.

In specific embodiment of the present invention any of the above methods additionally comprises the following step of isolating and purifying said protein of interest.

The invention further concerns a method of generating a recombinant host cell/production cell comprising:
a) transfecting a (mammalian) cell with the transcription unit or expression vector of the present invention, and
b) selecting a recombinant host cell/production cell.

The invention further concerns a kit comprising
a) a vector including at least one artificial intron sequence flanked by suitable recognition sites for restriction enzymes allowing the integration of a first and/or a second nucleotide sequence coding for at least a part of a gene of interest, and
b) instructions and optionally a vector map,
c) optionally a (eukaryotic) host cell.

Effectively the 2 nucleotide sequences in step a) are/become operatively linked.

The invention further concerns a kit comprising
a) a vector including at least parts of a transcription unit comprising a first nucleotide sequence comprising at least one artificial intron located within an immunoglobulin gene or parts of an immunoglobulin gene at the position of a native immunoglobulin intron, and whereby the nucleotide sequence of this transcription unit comprises suitable recognition sites for restriction enzymes allowing the integration of a second nucleotide sequence coding for another part of a gene of interest, and
b) instructions and optionally a vector map,
c) optionally a (eukaryotic) host cell.

Effectively the 2 nucleotide sequences in step a) are/become operatively linked.

The invention further concerns a kit comprising
a) a vector including at least parts of a transcription unit comprising a first polynucleotide sequence encoding a signal peptide sequence comprising at least one artificial intron located within said signal peptide gene sequence at the position of a native intron of this signal peptide gene sequence, and whereby the nucleotide sequence of this transcription unit comprises suitable recognition sites for restriction enzymes allowing the integration of a second nucleotide sequence coding for a gene of interest, and
b) instructions and optionally a vector map,
c) optionally a (eukaryotic) host cell.

Effectively the 2 nucleotide sequences in step a) are/become operatively linked.

In a specific embodiment of any of the above kits of the present invention said kit additionally comprises
a) a cultivation medium for the cultivation of a host cell, and/or
b) a selection medium for selecting and cultivating a transfected host cell.

In a further embodiment of the of any of the above kits of the present invention said kit comprises any one of the transcription units or expression vectors of the present invention, instructions, optionally a (eukaryotic) host cell and optionally a cell culture medium for cultivation of said cell, and optionally a selection medium for selecting and cultivating a transfected host cell.

The following examples are not limiting. They merely show possible embodiments of the invention. A person skilled in the art could easily adjust the conditions to apply it to other embodiments.

EXPERIMENTAL

Abbreviations

Figure 1:
FIG. 1: BASIC EXPRESSION VECTOR

AP: Alkaline phosphatase
ch: Chimeric
CH1: CH1 domain of immunoglobulin heavy chain
CH2: CH2 domain of immunoglobulin heavy chain
CH3: CH3 domain of immunoglobulin heavy chain
CHO: Chinese hamster ovary
CL: CL domain of IgG light chain
DHFR: Dihydrofolate reductase
ELISA: Enzyme-linked immunosorbant assay
h: Human
H: Hinge region of immunoglobulin heavy chain
HGH: Hamster growth hormone
HT: Hypoxanthine/thymidine
HRPO: Horseradish peroxidase
hu: Humanized
IgG: Immunoglobuline G
mAb: Monoclonal antibody
NPT: Neomycin phosphotransferase
PCR: Polymerase chain reaction
SEAP: Secreted alkaline phosphatase
VH: Variable region of IgG heavy chain
VL: Variable region of IgG light chain Materials and Methods Expression Vectors The Eukaryotic expression vector is a derivative of the pAD-CMV1 vector (WO 9201055) and mediate constitutive expression of the heterologous genes driven by the CMV promoter/enhancer. For termination and polyadenylation of the transcript of the gene of interest vectors contain the polyadenylation signal of the hamster growth hormone (SEQ ID NO: 8 in EP2009059399). The pBI-26 vector encodes a hamster-derived DHFR mini gene as amplifiable selection marker (see for example EP 0 393 438) (FIG. 1).

Genes of interest encoding for Fc fusion proteins are cloned into the vector using the multiple cloning sites located between promoter and polyadenylation signal. All recombinant expression vectors used as controls in the invention are summarized in FIG. 2. The genes are either cloned as cDNA or as genomic DNA versions. In the latter the intron and exon sequences of the constant domains are derived from the natural genomic gene sequences. The introns are in their natural positions located within the codon encoding for the first amino acid of the constant domain CH3 derived from a human IgG1. The gene structures of the various genes of interests are shown schematically in FIG. 2.

Cell Culture

CHO-DG44/dhfr$^{-/-}$ cells are maintained in suspension culture in the serum-free medium CHO-S-SFMII (Invitrogen) supplemented with hypoxanthine and thymidine (HT). Cells are incubated in cell culture flasks at 37° C. in a humidified atmosphere containing 5% $CO_2$. The cell number as well as the cell viability are determined with a Cedex (Innovatis AG, Germany) or via trypan blue dye exclusion. Cells are seeded at a concentration of $1-3\times10^5$ cells/mL in fresh medium every two to three days.

Transfections

Transfections of CHO-DG44 cells are conducted using Lipofectamine Plus reagent (Invitrogen). Per transfection $6\times10^5$ exponentially growing cells in 0.8 mL hypoxanthine/thymidine (HT)-supplemented CHO-S-SFMII medium (Invitrogen) are seeded in a well of a 6-well chamber. A mixture of plasmid DNA, 4 μL Lipofectamine® and 6 μL Plus™ reagent in a volume of 200 μL is generated for each transfection and added to the cells, following the protocol of the manufacturer. After incubation for 3 hours 2 mL of HT-supplemented CHO-S-SFMII medium is added. Transient transfections are performed in triplicate for each vector combination and supernatants are harvested 2 to 3 days post transfection.

ELISA

Titers of the Fc fusion proteins are quantified by ELISA with standard protocols using a mouse anti-human IgG (Fc specific) antibody (Sigma) and an HRP-conjugated goat anti-human IgG (Fc specific) antibody (Sigma). For detection the fast p-nitrophenyl phosphate tablet set (Sigma) or the TMB ELISA substrate (Serva) are used and the reaction is stopped either with NaOH (AP substrates) or $H_2SO_4$ (HRP substrates). Purified Fc fusion protein is used as standard. Samples are analyzed using an Infinite M200 Pro reader (TECAN, Crailsheim, Germany). Adsorptions are measured either at 405 nm (AP substrates) or 450 nm (HRP substrates).

SEAP Assay

SEAP activity is determined with the Great EscAPe™ SEAP Chemiluminescence Assay according to the protocol of the manufacturer (Clontech). Samples are analyzed using an Infinite M200 Pro reader (TECAN, Crailsheim, Germany).

EXAMPLES

Example 1

Cloning of Artificial Intron-Containing FC Fusion Genes

The first intron sequence (SEQ ID NO:1, FIG. 3A) is based on the intron sequence located between the variable and constant region of a human kappa gene. It is modified to introduce a single BglII restriction site close to the 5' end of the intron for cloning purposes introduce sequences which can act as stop codons in case of a non-splicing event of the messenger RNA and would lead to premature translation termination of the protein introduce a conserved branch site in the 3' region of the intron to allow for more efficient splicing.

The intron sequence is synthesized de novo at Invitrogen using the GENEART® technology.

Figure 4:
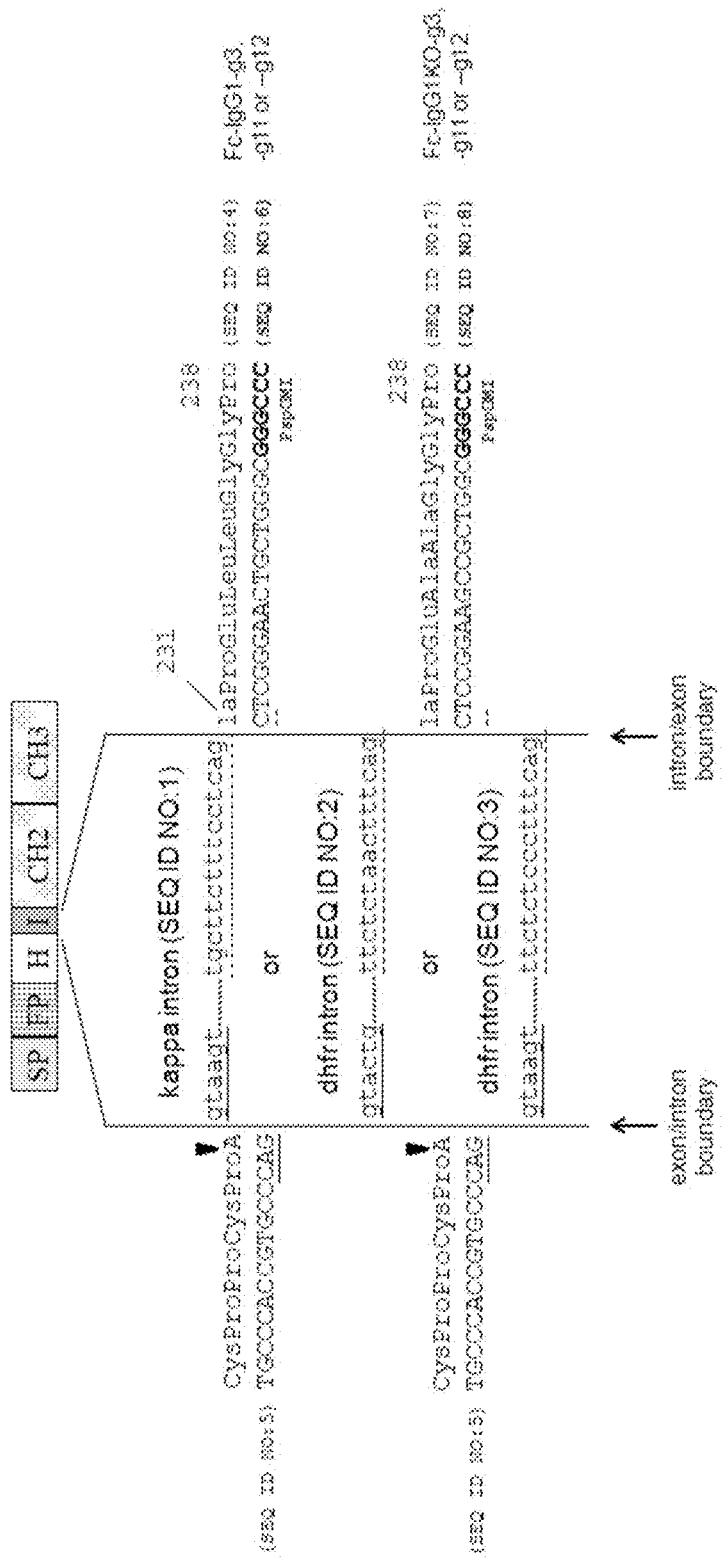
FIG. 4: POSITION OF ARTIFICIAL INTRONS IN SEQUENCE OF CH2 DOMAINS OF FC FUSION PROTEINS

For placement of the modified kappa intron within the constant domain CH2 of the Fc part of the Fc fusion proteins the cloning is done as follows. The intron sequence is amplified by PCR introducing via the PCR primers at the 5' ends of the intron sequence hinge coding sequences and a BamHI restriction site and at the 3' ends CH2 domain coding sequences followed by a PspOMI restriction site. In the following, the amplified fragments are cloned directionally into the BamHI and PspOMI digested expression vectors encoding the cDNA sequences of the Fc fusion protein genes shown schematically in FIG. 2. The resulting recombinant vectors encoding the Fc fusion proteins Fc-IgG1 and Fc-IgG1KO are marked with the suffix "g3" (see FIG. 4). The intron is placed within the codon for the first amino acid alanine of the constant domain CH2 at position 231 between the first and second nucleotide with a preceding codon for the amino acid proline at position 231 in such a way that a consensus splice donor and splice acceptor sequence is generated (FIG. 4).

The second intron sequence is isolated from the hamster dihydrofolate reductase gene (SEQ ID NO: 2, FIG. 3B). It is amplified from the eukaryotic expression vector pBI-26. This vector encodes a hamster-derived DHFR mini gene as amplifiable selection marker (see for example EP 0 393 438).

For placement of the dhfr intron within the constant domain CH2 of the Fc part of the Fc fusion proteins the cloning is done as follows. The intron sequence is amplified by PCR introducing via the PCR primers at the 5' ends of the intron sequence hinge coding sequences and a BamHI restriction site and at the 3' ends CH2 domain coding sequences followed by a PspOMI restriction site. In the following, the amplified fragments are cloned directionally into the BamHI and PspOMI digested expression vectors encoding the cDNA sequences of the Fc fusion protein genes shown schematically in FIG. 2. The resulting recombinant vectors encoding the Fc fusion proteins Fc-IgG1 and Fc-IgG1KO are marked with the suffix "g11" (see FIG. 4). The intron is placed within the codon for the first amino acid alanine of the constant domain CH2 at position 231 between the first and second nucleotide with a preceding codon for the amino acid proline at position 231 in such a way that a consensus splice donor and splice acceptor sequence is generated (FIG. 4).

The third intron sequence (SEQ ID NO:3) is based on the intron sequence isolated from the hamster dihydrofolate reductase gene (SEQ ID NO: 2) but is further modified to introduce a single BglII restriction site close to the 5' end of the intron for cloning purposes introduce optimized splice donor and acceptor sequences.

The intron sequence is synthesized de novo at Invitrogen using the GENEART® technology.

For placement of the modified dhfr intron within the CH2 domain of the Fc fusion proteins the same approach as described for the non-modified hamster dhfr intron (SEQ ID NO:2) is used. The resulting recombinant vectors encoding genes for the Fc fusion proteins Fc-IgG1 and Fc-IgG1KO are marked with the suffix "g12" (see FIG. 4). The intron is placed in all cases in such a way that consensus splice donor and splice acceptor sequences are generated.

Numbering of the amino acids of the constant domains and hinge regions of the heavy chains is according to the EU numbering in Kabat et al. (1991), "Sequences of proteins of immunological interest", US Dept. Health and Human Services.

Example 2

Impact of Artificial Introns on Expression of Fc Fusion Protein

To evaluate the impact of the intron sequence derived from the human kappa gene (SEQ ID NO: 1) on the expression if placed within the Fc exon region of an Fc fusion protein transient transfections are performed. Transient transfections allow assessment of the expression independent of chromosomal integration sites. The intron is placed in the codon for the first amino acid alanine at position 231 in the constant domain CH2 of the Fc region (see FIG. 4). CHO-DG44 cells are transfected with vectors encoding the various Fc fusion proteins ($13\times10^{10}$ molecules). This set-up is tested with a fusion protein consisting of the wild type Fc sequence of a human IgG1 or a Fc mutant with a Leu234Ala and Leu235Ala (according to EU numbering) substitution in the CH2 domain. As a control CHO-DG44 cells are transfected with vectors encoding either the cDNA of the respective Fc fusion protein or the genomic DNA with a natural intron within the codon for the first amino acid of the CH3 domains (see FIG. 2). Aside of the different gene formats the genetic set-ups of the various vectors for the expression of the various Fc fusion proteins are identical.

Supernatants are harvested 2 to 3 days post transfection and the titers of the Fc fusion proteins are determined using ELISA. Per vector combination 3 cell pools are transfected in each transfection series. Two independent transfection series for each set of Fc fusion proteins are performed. To correct for transfection efficiency cells are co-transfected with the plasmid pCMV-SEAP (100 ng DNA/transfection reaction), which encodes the secreted alkaline phosphatase, and the SEAP activity is measured.

FIG. 5 shows the data of 2 independent transient transfection series performed in triplicate. Surprisingly, the artificial intron-containing gene set-ups in which a modified single intron sequence derived from a human kappa gene (SEQ ID NO: 1, FIG. 3A) is placed in a new position within the Fc fusion gene are outperforming the corresponding cDNA versions by a factor of 1.8-2. In contrast, cells transfected with the genomic DNA with a native intron within the CH3 domains as in the natural immunoglobulin genes show an expression performance comparable to the cDNA setting or even lower.

The invention claimed is:

1. A transcription unit or expression vector comprising a gene of interest and comprising at least one artificial intron, whereby the artificial intron is
   i. replacing a native intron sequence within said gene of interest, or
   ii. positioned at the site of a native intron position within said gene of interest, wherein the gene of interest is an immunoglobulin gene.

2. The transcription unit or expression vector of claim 1, wherein the artificial intron sequence comprises a nucleotide sequence at least 95% identical to SEQ ID NO: 1, SEQ ID NO: 2 or SEQ ID NO:3, and wherein presence of the artificial intron sequence enhances expression of the gene of interest as compared to expression of gene of interest without the artificial intron sequence.

3. The transcription unit or expression vector of claim 1, wherein the artificial intron sequence is SEQ ID NO: 1, SEQ ID NO: 2 or SEQ ID NO:3.

4. The transcription unit or expression vector of claim 1, wherein said artificial intron is operably linked to a heterologous coding sequence of a gene.

5. The transcription unit or expression vector of claim 1, wherein the gene of interest is an immunoglobulin gene encoding an IgG1, IgG2, or IgG4.

6. The transcription unit or expression vector of claim 1, wherein the gene of interest encodes at least one domain of an immunoglobulin gene.

7. The transcription unit or expression vector of claim 6, wherein said domain is a variable domain.

8. The transcription unit or expression vector of claim 6, wherein said domain is a constant domain of an immunoglobulin gene or a hinge region of an immunoglobulin gene.

9. The transcription unit or expression vector of claim 5, wherein the artificial intron is located within the codon encoding the first amino acid at position 108 in the constant domain CL of immunoglobulin kappa and lambda light chains between the first and second nucleotide of the codon, within the codon encoding the first amino acid at position 118 in the constant domain CH1 of immunoglobulin heavy chains between the first and second nucleotide of the codon, within the codon encoding the first amino acid at position 216 in the hinge region of immunoglobulin heavy chains between the first and second nucleotide of the codon, within the codon encoding the first amino acid at position 231 in the constant domain CH2 of immunoglobulin heavy chains between the first and second nucleotide of the codon and/or within the codon encoding the first amino acid at position 341 in the constant domain CH3 of immunoglobulin heavy chains between the first and second nucleotide of the codon.

10. The transcription unit or expression vector of claim 1, wherein the gene of interest is an Fc-fusion protein.

11. The transcription unit or expression vector of claim 10, wherein the artificial intron is located within the codon encoding the first amino acid at position 216 in the hinge region of an immunoglobulin heavy chain between the first and second nucleotide of the codon if part of the Fc-fusion protein, within the codon encoding the first amino acid at position 231 in the constant domain CH2 of an immunoglobulin heavy chain between the first and second nucleotide of the codon and/or within the codon encoding the first amino acid at position 341 in the constant domain CH3 of an immunoglobulin heavy chain between the first and second nucleotide of the codon.

12. The transcription unit or expression vector of claim 1, wherein the artificial intron is positioned in a signal peptide sequence operably linked to a heterologous coding sequence of a gene.

13. The transcription unit or expression vector according to claim 12, wherein the signal peptide is a signal peptide of an immunoglobulin gene.

14. The transcription unit or expression vector according to claim 13, wherein the artificial intron is located within the codon encoding the amino acid at position −4 counting backwards from the 3′ end of the amino acid sequence of the signal peptide of the signal peptide sequence of immunoglobulin heavy and/or light chains between the first and second nucleotide of the codon.

15. The transcription unit or expression vector of claim 1, wherein the artificial intron is positioned within the nucleotide sequence successions CAG:C, CAG:T, AAG:C, AAG:T, TAG:T or TAG:C, preferably CAG:C, CAG:T, AAG:C or AAG:T, whereby the colons denote the site of intron insertion, and one of the following amino acid pairs is encoded at the intron insertion site:

| CAG:C | CAG:T | AAG:C | AAG:T | TAG:C | TAG:T |
|---|---|---|---|---|---|
| GlnLeu CAGCTN | GlnPhe CAGTTY | LysLeu AAGCTN | LysPhe AAGTTY | PheSer TTTAGC | PheSer TTTAGT |
| GlnPro CAGCCN | GlnLeu CAGTTR | LysPro AAGCCN | LysLeu AAGTTR | SerSer TCTAGC | SerSer TCTAGT |
| GlnHis CAGCAY | GlnSer CAGTCN | LysHis AAGCAY | LysSer AAGTCN | TyrSer TATAGC | TyrSer TATAGT |
| GlnGln CAGCAR | GlnTyr CAGTAY | LysGln AAGCAR | LysTyr AAGTAY | CysSer TGTAGC | CysSer TGTAGT |
| GlnArg CAGCGN | GlnCys CAGTGY | LysArg AAGCGN | LysCys AAGTGY | LeuSer CTTAGC | LeuSer CTTAGT |
| SerAla TCAGCN | GlnTrp CAGTGG | GlnAla CAAGCN | LysTrp AAGTGG | ProSer CCTAGC | ProSer CCTAGT |
| ProAla CCAGCN | SerVal TCAGTN | LysAla AAAGCN | GlnVal CAAGTN | HisSer CATAGC | HisSer CATAGT |
| ThrAla ACAGCN | ProVal CCAGTN | GluAla GAAGCN | LysVal AAAGTN | ArgSer CGTAGC | ArgSer CGTAGT |
| AlaAla GCAGCN | ThrVal ACAGTN | LeuSer YTAAGC | GluVal GAAGTN | IleSer ATTAGC | IleSer ATTAGT |
| PheSer TTCAGC | AlaVal GCAGTN | SerSer TCAAGC | LeuSer YTAAGT | ThrSer ACTAGC | ThrSer ACTAGT |
| SerSer TCCAGC | PheSer TTCAGT | ProSer CCAAGC | SerSer TCAAGT | AsnSer AATAGC | AsnSer AATAGT |
| TyrSer TACAGC | SerSer TCCAGT | GlnSer CAAAGC | ProSer CCAAGT | SerSer AGTAGC | SerSer AGTAGT |
| CysSer TGCAGC | TyrSer TACAGT | ArgSer MGAAGC | GlnSer CAAAGT | ValSer GTTAGC | ValSer GTTAGT |
| LeuSer CTCAGC | CysSer TGCAGT | IleSer ATAAGC | ArgSer MGAAGT | AlaSer GCTAGC | AlaSer GCTAGT |
| ProSer CCCAGC | LeuSer CTCAGT | ThrSer ACAAGC | IleSer ATAAGT | AspSer GATAGC | AspSer GATAGT |
| HisSer CACAGC | ProSer CCCAGT | LysSer AAAAGC | ThrSer ACAAGT | GlySer GGTAGC | GlySer GGTAGT |
| ArgSer CGCAGC | HisSer CACAGT | ValSer GTAAGC | LysSer AAAAGT | LeuAla YTAGCN | LeuVal YTAGTN |
| IleSer ATCAGC | ArgSer CGCAGT | AlaSer GCAAGC | ValSer GTAAGT | IleAla ATAGCN | IleVal ATAGTN |
| ThrSer ACCAGC | IleSer ATCAGT | GluSer GAAAGC | AlaSer GCAAGT | ValAla GTAGCN | ValVal GTAGTN |
| AsnSer ATCAGC | ThrSer ACCAGT | GlySer GGAAGC | GluSer GAAAGT | | |
| SerSer AGCAGC | AsnSer AACAGT | | GlySer GGAAGT | | |
| ValSer GTCAGC | SerSer AGCAGT | | | | |
| AlaSer GCCAGC | ValSer GTCAGT | | | | |
| AspSer GACAGC | AlaSer GCCAGT | | | | |
| GlySer GGCAGC | AspSer GACAGT | | | | |
| | GlySer GGCAGT. | | | | | colon: site of intron insertion, N = any base, Y = C or T, R = A or G, M = C or A 16. A host cell comprising the expression vector of claim 1.

17. The host cell of claim 16, wherein said cell is a eukaryotic cell.

18. A kit comprising
a) a vector including a transcription unit comprising a first nucleotide sequence comprising at least one artificial intron located within an immunoglobulin gene or at the position of a native immunoglobulin intron, and wherein the nucleotide sequence of the transcription unit comprises recognition sites for restriction enzymes allowing integration of a second nucleotide sequence coding for another a gene of interest,
b) instructions,
c) optionally a vector map, and
d) optionally a host cell.

19. A kit comprising
a) a vector including a transcription unit comprising a first polynucleotide sequence encoding a signal peptide sequence comprising at least one artificial intron boated within said signal peptide sequence at the position of a native intron of the signal peptide gene sequence, and wherein the nucleotide sequence of the transcription unit comprises recognition sites for restriction enzymes allowing integration of a second nucleotide sequence coding for a gene of interest, b) instructions,
c) optionally a vector map, and
d) optionally a host cell.

20. The kit of claim 18 additionally comprising
a) a cultivation medium for the cultivation of a host cell, and/or
b) a selection medium for selecting and cultivating a transfected host cell.

\* \* \* \* \*

```
                              SEQUENCE LISTING

<160> NUMBER OF SEQ ID NOS: 22

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      intron polynucleotide derivative derived from
      genomic region of human kappa light chain and
      further modified

<400> SEQUENCE: 1
gtaagtgcac tttcctaata gatctaattc taaactctga gggggtcgga tgacgtggcc      60
attctttgcc taaagcattg agtttactgc aaggtcagaa aagcatgcaa agccctcaga     120
atggctgcaa agagctccaa caaaacaatt tagaacttta ttaaggaata gggggaagct     180
aggaagaaac tcaaaacatc aagattttaa atacgcttct tggtctcctt gctataatta     240
tctgggataa gcatgctgtt ttctgtctgt ccctaacatg ccctgtgatt atccgcaaac     300
aacacaccca agggcagaac tttgttatac taacaccatc ctgtttgctt ctttcctcag     360

<210> SEQ ID NO 2
<211> LENGTH: 304
<212> TYPE: DNA
<213> ORGANISM: Cricetulus griseus
<220> FEATURE:
<223> OTHER INFORMATION: Intron sequence derived from genomic region of
      hamster dihydrofolate reductase

<400> SEQUENCE: 2
gtactggctg gattgggtta gggaaaccga ggcggttcgc tgaatcgggt cgagcacttg      60
gcggagacgc gcgggccaac tacttaggga cagtcatgag gggtaggccc gccggctgct     120
gcccttgccc atgcccgcgg tgatccccat gctgtgccag cctttgccca gaggcgctct     180
agctgggagc aaagtccggt cactgggcag caccaccccc cggacttgca tgggtagccg     240
ctgagatgga gcctgagcac acgtgacagg gtccctgtta acgcagtgtt tctctaactt     300
tcag                                                                 304

<210> SEQ ID NO 3
<211> LENGTH: 308
<212> TYPE: DNA
<213> ORGANISM: Artificial Sequence
<220> FEATURE:
<223> OTHER INFORMATION: Description of Artificial Sequence: Synthetic
      intron polynucleotide derived from genomic region of hamster
      dihydrofolate reductase and further modified

<400> SEQUENCE: 3
gtaagtgctg gattgggtta gatctggaaa ccgaggcggt tcgctgaatc gggtcgagca      60
```

```
cttggcggag acgcgcgggc caactactta gggacagtca tgaggggtag gcccgccggc    120
tgctgccctt gcccatgccc gcggtgatcc ccatgctgtg ccagcctttg cccagaggcg    180
ctctagctgg gagcaaagtc cggtcactgg gcagcaccac cccccggact tgcatgggta    240
gccgctgaga tggagcctga gcacacgtga cagggtccct gttaacgcag tgtttctctc    300
cctttcag                                                            308
```

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Pro Pro Cys Pro Ala Pro Glu Leu Leu Gly Gly Pro
1               5                   10

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
tgcccaccgt gcccag                                                    16
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
ctcgggaact gctgggcggg ccc                                            23
```

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Pro Pro Cys Pro Ala Pro Glu Ala Ala Gly Gly Pro
1               5                   10

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
ctccggaagc cgctggcggg ccc                                            23
```

```
<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Thr Ala Gly Val Leu Ser
1               5

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcaggaactg cag                                                          13

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgtcctctc t                                                            11

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Leu Leu Leu Val Ser Ala Gly
1               5

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctgctacttc tag                                                          13

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tttcagctgg c                                                            11
```

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Val Ser Ser Ala Ser Thr Lys
1               5

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
accgtctctt cag                                                          13

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctccaccaa g                                                            11

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Glu Ile Lys Arg Thr Val Ala
1               5

<210> SEQ ID NO 19
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtggagatca aac                                                          13

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaactgtggc t                                                            11

```
<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: This region may encompass 11-40 nucleotides,
      wherein some positions may be absent
<220> FEATURE:
<221> NAME/KEY: modified_base
<222> LOCATION: (41)..(41)
<223> OTHER INFORMATION: a, c, t, g, unknown or other

<400> SEQUENCE: 21
yyyyyyyyyy yyyyyyyyyy yyyyyyyyyy yyyyyyyyyy nyagr                45

<210> SEQ ID NO 22
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This region may encompass 100-200 nucleotides,
      wherein some positions may be absent

<400> SEQUENCE: 22
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa                                                 200
```